United States Patent
Huang et al.

(10) Patent No.: US 7,741,357 B1
(45) Date of Patent: Jun. 22, 2010

(54) HETEROCYCLIC AND CARBONATE DERIVATIVES OF NDGA AND THEIR USE AS NEW ANTI-HIV AND ANTI-CANCER AGENTS

(75) Inventors: Ru Chih C. Huang, Baltimore, MD (US); Apostolos Gittis, Baltimore, MD (US); Evangelos Moudrianakis, Baltimore, MD (US); Julie A. Dohm, Oak Lawn, IL (US); Jih Ru Hwu, Hsinchu (TW); Ming-Hua Hsu, Hsinchu (TW)

(73) Assignee: Johns Hopkins University, Baltimore, MD (US)

( * ) Notice: Subject to any disclaimer, the term of this patent is extended or adjusted under 35 U.S.C. 154(b) by 206 days.

(21) Appl. No.: 11/783,970

(22) Filed: Apr. 13, 2007

Related U.S. Application Data

(60) Provisional application No. 60/792,332, filed on Apr. 17, 2006.

(51) Int. Cl.
*A01N 43/36* (2006.01)
(52) U.S. Cl. ............ 514/408; 514/231.2; 514/315; 548/400; 548/560; 544/106; 546/184
(58) Field of Classification Search .......... None
See application file for complete search history.

(56) References Cited

FOREIGN PATENT DOCUMENTS

JP  EP 0541112 B1 * 12/1993
WO  WO 8801509 * 3/1988

OTHER PUBLICATIONS

Wolff, Manfred, "Burger's Medicinal Chemistry", 4th Ed., Part I, John Wiley, NY (1980).*
Dohm et al. (J. Mol. Biol. 2005; 349(4): p. 731-744).*

* cited by examiner

*Primary Examiner*—Kamal A Saeed
*Assistant Examiner*—Valerie Rodriguez-Garcia
(74) *Attorney, Agent, or Firm*—Venable LLP; Ann S. Hobbs

(57) ABSTRACT

Reaction of nordihydroguaiaretic acid with various alkyl chlorides, 1-piperidinecarbonyl chloride, methyl chloroformate, or 1,1'-carbonyldiimidazole under alkaline conditions produced the corresponding phenol ethers, carbamates and carbonates, respectively, in 67-83% yields (Scheme 1 and Scheme 2). Among these derivatives, the nitrogen-containing compounds were converted to the corresponding hydrochloride salts. Having good solubility, these NDGA derivatives were found to be stable in aqueous solution. These new compounds exerted potent activities against HIV Tat-regulated transactivation in cos-7 cells. The most active transcription inhibitor compound of this series 5b ($P_4N$, Tetrapiperidino NDGA, meso-2,3-dimethyl-1,4-bis(3,4-[2-(piperidino)ethoxyphenyl])butane tetrakishydrochloride salt) has an $IC_{50}$ of 0.88 μM.

10 Claims, 11 Drawing Sheets

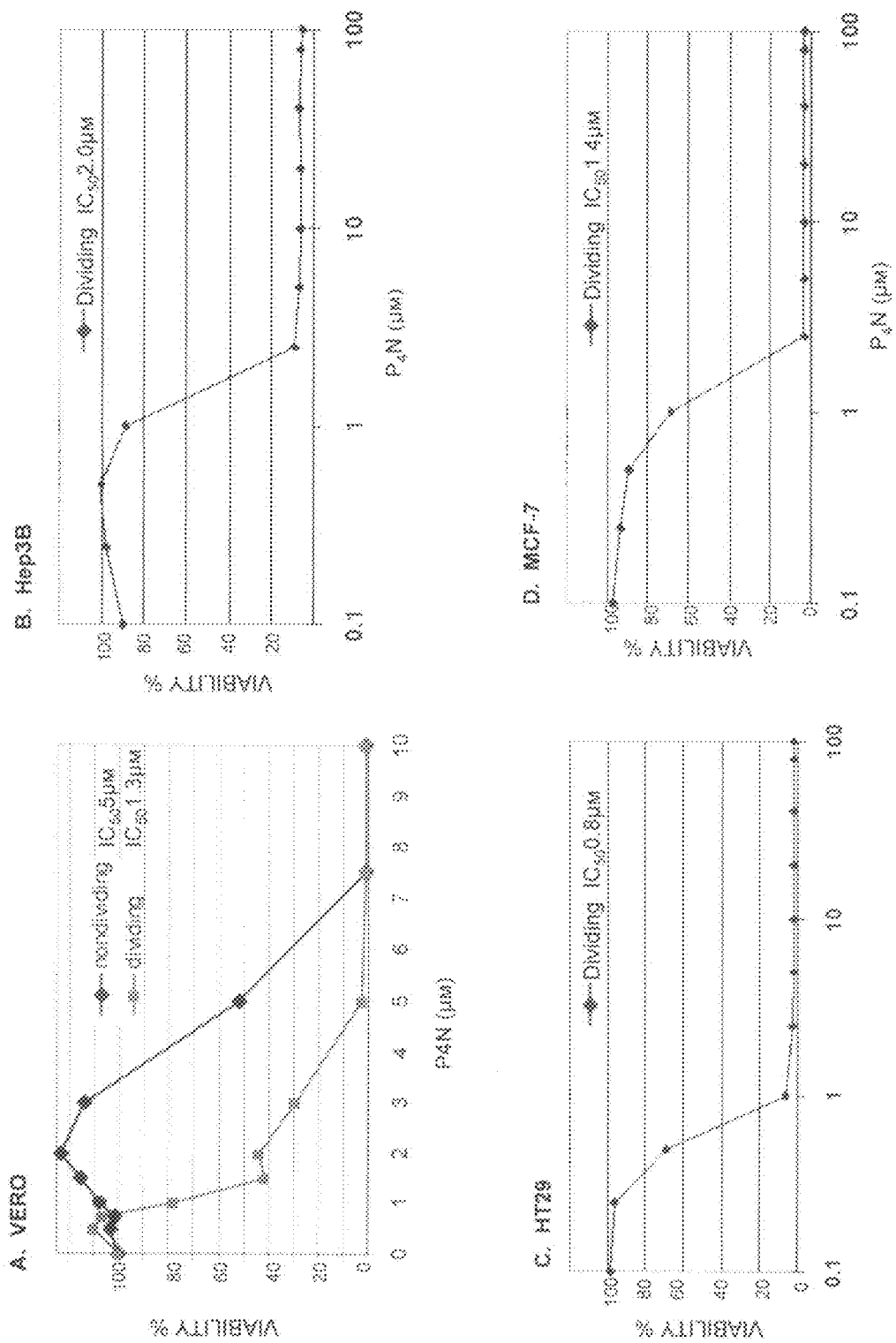

SEQUENCE LISTING

```
<160> NUMBER OF SEQ ID NOS: 3

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gatgggcggg acg                                                          13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtcccgccc atc                                                          13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcctggcggg gct                                                          13
```

HETEROCYCLIC AND CARBONATE DERIVATIVES OF NDGA AND THEIR USE AS NEW ANTI-HIV AND ANTI-CANCER AGENTS

CROSS REFERENCE TO RELATED APPLICATIONS

This application claims priority to U.S. Provisional application No. 60/792,332, filed Apr. 17, 2006, which is incorporated herein by reference in its entirety.

FIELD OF THE INVENTION

The invention relates to nordihydroguaiaretic acid derivatives particularly useful for treating viral infections and tumors.

BACKGROUND

Nordihydroguaiaretic acid (NDGA, 1) is a lignan found in the leaves and twigs of the shrub *Larrea tridentata*. Being a lipoxygenases inhibitor, NDGA can induce cystic nephropathy in the rat.[1] In addition, it shows various bioactivities, including inhibition of protein kinase C,[2] induction of apoptosis,[3] alterations of membrane,[4] elevation of cellular $Ca^{2+}$ level[5] and activation of $Ca^{2+}$ channels in smooth muscle cells,[6] breakdown of pre-formed Alzheimer's beta-amyloid fibrils in vitro,[7] anti-oxidation,[8] etc. This natural product is used commercially as a food additive to preserve fats and butter in some parts of the world. Recently, the derivatives of the plant lignan NDGA have been used to block viral replication through the inhibition of viral transcription.[9-16] These compounds can inhibit production of HIV,[9-13] herpes simplex virus,[14-15] and HPV transcripts[16] by deactivation of their Sp1-dependent promoters. Moreover, (tetra-O-methyl)nordihydroguaiaretic acid ($M_4N$, EM1421 2) can function as an anti-HIV proviral transcription inhibitor and causes growth arrest of a variety of transformed human and mouse cells in culture and in mice.[17,18,22] Compound $M_4N$ (EM1421) is currently in clinical trials against human cancers.[23]

While $M_4N$ (2) is a strikingly effective and non-toxic anti-cancer agent, $M_4N$ and several other methylated NDGAs, all show poor water solubility which somewhat limit their applicabilities for certain drug action studies. To circumvent this problem, a water soluble derivative of NDGA, (tetra-O-dimethylglycyl)nordihydroguaiaretic acid ($G_4N$, 4) has been designed and synthesized.[11] $G_4N$ is a very effective mutation-insensitive inhibitor to HIV-1, HSV-1 and HSV-2.[10,15] However, it is somewhat unstable and has a relatively short half-life in aqueous solution, reportedly due to the ester bonds connecting the dimethyl glycine moieties onto the NDGA main skeleton.[11]

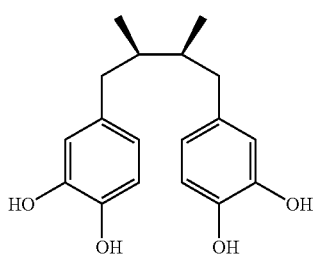

1 (NDGA)

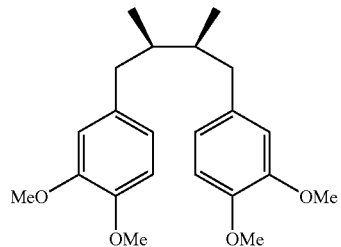

2 ($M_4N$ EM1421)

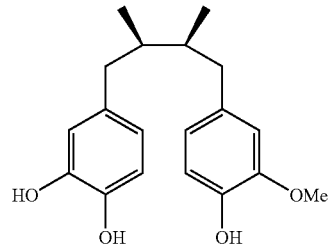

3 (Mal.4)

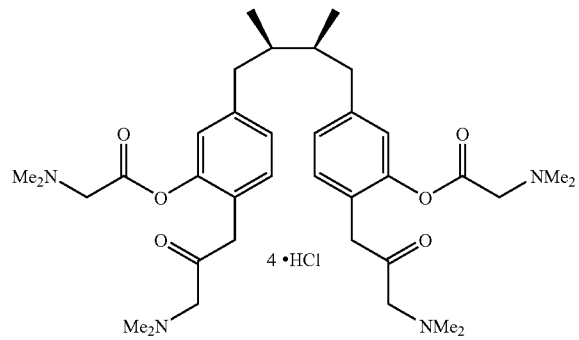

4 ($G_4N$)

4 •HCl

Therefore, there is a need for NDGA derivatives with improved water solubility and stability having the desired pharmaceutical effects. Accordingly, we have developed new derivatives of NDGA that have these advantages and will be useful in therapeutic compositions and treatment methods. We describe herein the chemical synthesis of these new compounds and their efficacies.

SUMMARY

The present invention provides compounds, pharmaceutical compositions, methods and kits for the treatment of diseases and disorders, in particular, viral infections, and proliferative diseases such as tumors. Described herein are new compounds of formula

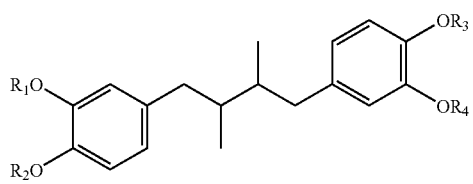

wherein
wherein $R_1$-$R_4$ are independently selected from the group consisting of:

(a) a straight chain or branched lower alkyl group substituted with a heterologous nitrogen-containing ring group of five to seven members;

(b) in combination with the O attached to the phenyl ring, a carbamate group other than a methyl carbamate group, optionally containing a five or six membered carbon-nitrogen ring;

(c) in combination with the O attached to the phenyl ring, a $C_1$-$C_6$ straight chain or branched carbonate group; and (d) wherein $R_1$ and $R_2$; or $R_3$ and $R_4$; or $R_1$ and $R_2$, and $R_3$ and $R_4$; together with the phenyl group to which they are attached, combine to form a cyclic carbonate group other than meso-2,3-dimethyl-1,4-bis(benzo[d][1,3]dioxol-2-one)butane; and salts of the compounds.

Examples of such compounds are meso-2,3-dimethyl-1,4-bis(3,4-[2-(pyrrolidino)ethoxyphenyl])butane, meso-2,3-dimethyl-1,4-bis(3,4-[2-(piperidino)ethoxyphenyl])butane, meso-2,3-dimethyl-1,4-bis(3,4-[2-(morpholino)ethoxyphenyl])butane, meso-2,3-dimethyl-1,4-bis(3,4-[3-(morpholino)propoxyphenyl])butane, meso-2,3-dimethyl-1,4-bis[3,4-(phenyl piperidine-1-carboxylate)]butane, meso-2,3-dimethyl-1,4-bis[3,4-(methyl phenyl carbonate)]butane, and meso-2,3-dimethyl-1,4-bis(benzo[d][1,3]dioxol-2-one)butane.

Substitutions on the heterologous rings may include halogens, lower alkyl and/or alkoxy groups.

Pharmaceutical compositions described herein contain a substantially pure preparation of at least one such NDGA derivative in a pharmaceutically acceptable carrier or excipient.

Thus, included are pharmaceutical compositions comprising a pharmaceutically acceptable carrier or excipient and at least one compound of formula

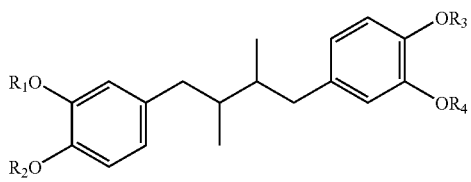

wherein $R_1$-$R_4$ are independently selected from the group consisting of:

(a) a straight chain or branched lower alkyl group substituted with a heterologous nitrogen-containing ring group of five to seven members;

(b) in combination with the O attached to the phenyl ring, a carbamate group, other than a methyl carbamate group, optionally containing a five or six membered carbon-nitrogen ring;

(c) in combination with the O attached to the phenyl ring, a $C_1$-$C_6$ straight chain or branched carbonate group; and (d) wherein $R_1$ and $R_2$; or $R_3$ and $R_4$; or $R_1$ and $R_2$, and $R_3$ and $R_4$; together with the phenyl group to which they are attached, combine to form a cyclic carbonate group;

or a salt of the compound.

The above-mentioned compositions are used in a method of treatment of a disease or disorder in a subject comprising administering to the subject an effective amount of the composition to treat the disease or disorder. Diseases and disorders to be treated include, inter alia, viral and proliferative diseases (e.g. cancer), as mentioned in detail below.

According to the methods described herein, the compounds and pharmaceutical compositions are administered to an individual in need of treatment, especially a mammal (e.g. a human), in amounts effective for treating a disease or disorder with which the individual is afflicted.

The above-mentioned compounds are also useful in methods of inhibiting expression of a Sp1-regulated eukaryotic gene in a mammalian cell or subject, of inhibiting HIV Tat-regulated transactivation in a cell or subject, and of widening the major groove of a double stranded deoxyoligonucleotide containing an Sp1 binding site '5GGGCGGG3' (dsOLIGO$_{sp}$). As such, they will be useful in methods for treating diseases and disorders involving these processes, as described in further detail below.

BRIEF DESCRIPTION OF THE DRAWINGS

FIG. 11: Effect of $P_4N$ on Proliferation of VERO Cells and Three Human Cancer Cells in Culture.

DETAILED DESCRIPTION

Figure 1:
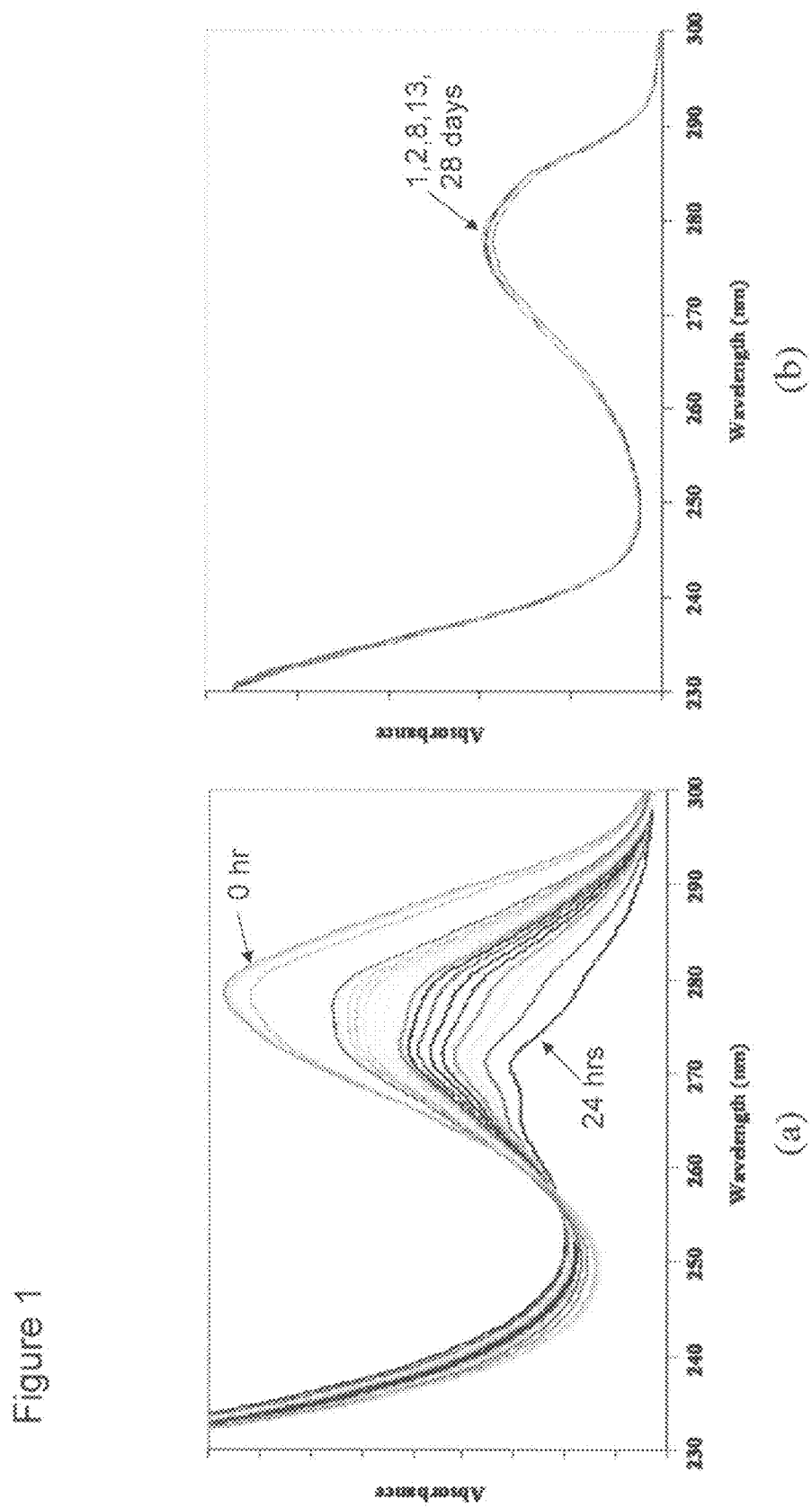
FIG. 1: Stability of Two NDGA Derivatives $G_4N$ and $P_4N$ (HCl salts) in Aqueous Solution. Time Dependent Changes in UV spectra showing (a) $G_4N$ is unstable and (b) meso-2,3-dimethyl-1,4-bis(3,4-[2-piperidino)ethoxyphenyl])butane ($P_4N$) (compound 5b in Scheme 1) (day 1, 2, 8, 13, 28) is stable in Milli-Q water after 28 days at 20° C.

The invention described below is given by way of example only and is not to be interpreted in any way as limiting the invention.

The present inventors have surprisingly discovered that the compounds and compositions containing the NDGA derivatives described herein are particularly effective for the treatment of viral infection and proliferative diseases such as tumors. In addition to the properties of improved water solubility (Scheme 1 compounds) and stability, the compounds should be suitable for systemic treatment. Although not wishing to be bound by any particular theory, it is believed that these compounds are advantageous in that they exert their pharmaceutical effects by binding to the Sp1 binding site in a reversible manner, thus causing less systemic toxicity, while still exhibiting good efficacy against the targeted disease or disorder.

DEFINITIONS

As used herein, the term "lower alkyl" means $C_1$-$C_6$ alkyl.

As used herein, the term "lower alkyoxy" means $C_1$-$C_6$ alkoxy.

As used herein, "heterologous ring" means a 5-7 membered carbon-nitrogen or carbon-oxygen ring.

As used herein, the term "NDGA derivative" refers to a derivative of NDGA having the formula:

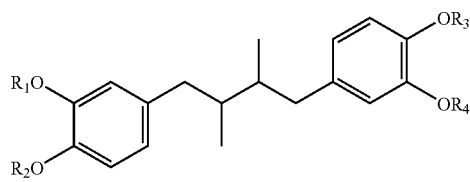

wherein wherein $R_1$-$R_4$ are independently selected from the group consisting of:

(a) a straight chain or branched lower alkyl group substituted with a heterologous nitrogen-containing ring group of five to seven members such as a pyrrolidino, piperidino, or morpholino group;

(b) in combination with the O attached to the phenyl ring, a carbamate group, other than a methyl carbamate group, optionally containing a five or six membered carbon-nitrogen ring;

(c) in combination with the O attached to the phenyl ring, a $C_1$-$C_6$ straight chain or branched carbonate group; and (d) wherein $R_1$ and $R_2$; or $R_3$ and $R_4$; or $R_1$ and $R_2$, and $R_3$ and $R_4$; together with the phenyl group to which they are attached, combine to form a cyclic carbonate group;

or a salt of the compound.

By "carbamate" is meant a substituent, in combination with the O attached to the phenyl ring, of the group —O—C(O)—NHR, or —O—C(O—NR$_5$R$_6$, wherein R, $R_5$ or $R_6$ represent any carbon-containing group as further defined herein, or wherein $R_5$ and $R_6$ together complete a nitrogen-containing ring.

By "carbonate" is meant a substituent, in combination with the O attached to the phenyl ring, of the group —O—CO—OR, wherein R represents any carbon-containing group as further defined herein.

As used herein, "buffers" includes any buffer conventional in the art, such as, for example, Tris, phosphate, imidazole, and bicarbonate.

As used herein, "target tissue" means any tissue to which it is desired to deliver an effective concentration of a compound of the invention, e.g., blood, brain, a specific tumor.

As used herein, the terms "treatment," "treating," and the like, refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse affect attributable to the condition or disease. "Treatment," thus, for example, covers any treatment of a condition or disease in a mammal, particularly in a human, and includes: (a) preventing the condition or disease from occurring in a subject which may be predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease.

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed, and is compatible with other ingredients of the formulation. For example, the carrier for a formulation containing the present compounds preferably does not include oxidizing agents and other compounds that are known to be deleterious to such. Suitable carriers include, but are not limited to, water, dextrose, glycerol, saline, ethanol, buffer, dimethyl sulfoxide, Cremaphor EL, and combinations thereof. The carrier may contain additional agents such as wetting or emulsifying agents, or pH buffering agents. Other materials such as antioxidants, humectants, viscosity stabilizers, and similar agents may be added as necessary.

Pharmaceutically acceptable salts herein include the acid addition salts which are formed with inorganic acids such as, for example, hydrochloric or phosphoric acids, or such organic acids as acetic, mandelic, oxalic, and tartaric. Salts may also be derived from inorganic bases such as, for example, sodium, potassium, ammonium, calcium, or ferric hydroxides, and such organic bases as isopropylamine, trimethylamine, 2-ethylamino ethanol, and histidine.

The term "pharmaceutically acceptable excipient," includes vehicles, adjuvants, or diluents or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

The terms "individual", "subject," "host," and "patient," are used interchangeably herein to refer to an animal being treated with the present compositions, including, but not limited to, simians, humans, felines, canines, equines, bovines, porcines, ovines, caprines, mammalian farm animals, mammalian sport animals, and mammalian pets.

As used herein "parenteral administration" herein means intravenous, intra-arterial, intramuscular, subcutaneous, transdermal, intradermal and intraperitoneal administration.

A "substantially purified" compound in reference to the compounds described herein is one that is substantially free of compounds that are not the compound in question. By "substantially free" is meant at least 50%, preferably at least 70%, more preferably at least 80%, and even more preferably at least 90%, most preferably greater than 95% or 99% free of extraneous materials.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the singular forms "a", "an", and "the" include plural referents unless the context clearly dictates otherwise. Thus, for example, reference to "a compound" includes a plurality of such compounds and equivalents thereof known to those skilled in the art.

Compounds disclosed herein may be made by the methods described herein, or by any other methods that will be known to those of skill in the art.

Overview of Synthesis of NDGA Derivatives. Exemplary compounds of the present invention were prepared by treating NDGA (1) with an alkyl chloride bearing a hydrocarbon spacer and a nitrogen-containing five- or six-membered ring in the presence of sodium carbonate and acetone (see Scheme 1). These intermediates were then allowed to react with $HCl_{(g)}$ in situ to give tetra-O-alkylated NDGA 5a-d in 67-82% overall yields. Their solubility in aqueous solution was found 379-541 mg/mL.

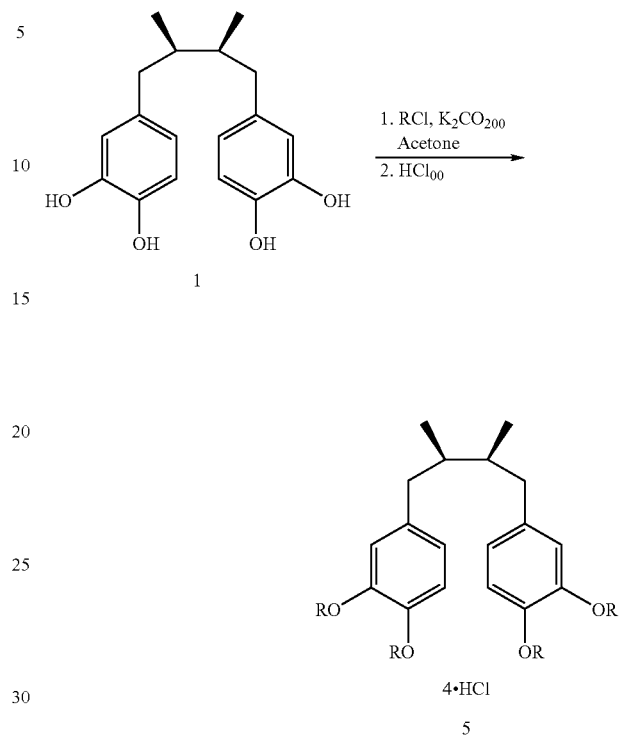

Scheme 1

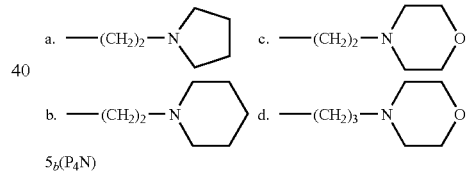

Several new lipophilic NDGA derivatives in the families of carbamate and carbonate were prepared as shown in Scheme 2. Treatment of NDGA with 1-piperidinecarbonyl chloride in the presence of pyridine at 0° C. produced the NDGA carbamate 6a in 72% yield. Under the same conditions, NDGA reacted with methyl chloroformate or 1,1'-carbonyldiimidazole afforded carbonates 6b and 7, respectively. The latter product was generated through an intramolecular cyclization process.

The new NDGA derivatives (Scheme 1) were found stable in aqueous solution; >99% of these compounds remained intact after 28 days (see FIG. 1($b$)). In a sharp contrast, >96% $G_4N$ (4) decomposed in aqueous solution within 24 h (see FIG. 1($a$)).

Scheme 2

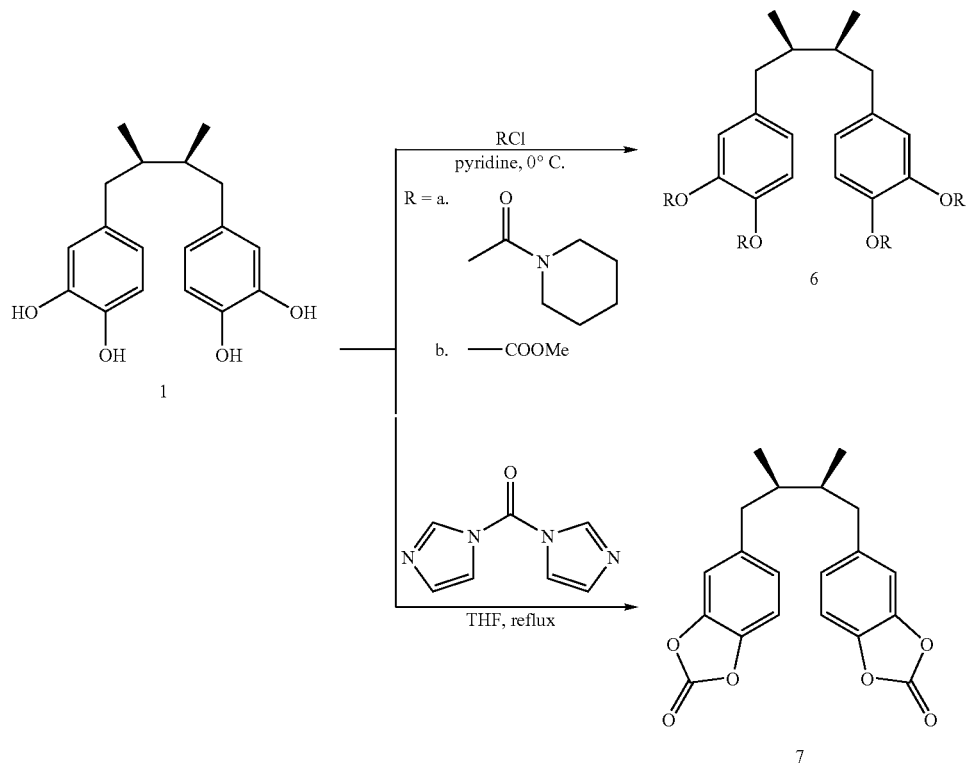

General Procedure. All reactions were carried out in oven-dried glassware (120° C.) under an atmosphere of nitrogen, unless as indicated otherwise. Acetone, dichloromethane, 1,4-dioxane, ethyl acetate, hexane, and tetrahydrofuran were purchased Mallinckrodt Chemical Co. Acetone was dried with 4 Å molecular sieves and distilled. Dichloromethane, ethyl acetate, and hexane were dried and distilled from $CaH_2$. 1,4-Dioxane and tetrahydrofuran were dried by distillation from sodium and benzophenone under an atmosphere of nitrogen. Nordihydroguaiaretic acid was purchased from Fluka Chemical Co. 4-(2-Chloroethyl)morpholine hydrochloride, 1-(2-chloroethyl)piperidine monohydrochloride, 1-(2-chloroethyl)pyrrolidine hydrochloride, N,N'-dicyclohexylcarbodiimide (DCC), 4-dimethylaminopyridine (DMAP), and potassium carbonate were purchased from Aldrich Chemical Co.

The melting point was obtained with a Buchi 535 melting point apparatus. Analytical thin layer chromatography (TLC) was performed on precoated plates (silica gel 60 F-254), purchased from Merck Inc. Gas chromatographic analyses were performed on a Hewlett-Packard 5890 Series II instrument equipped with a 25-m crosslinked methyl silicone gum capillary column (0.32 mm i.d.). Nitrogen gas was used as a carrier gas and the flow rate was kept constant at 14.0 mL/min. The retention time $t_R$ was measured under the following conditions: injector temperature 260° C., isothermal column temperature 280° C. Gas chromatography and low resolution mass spectral analyses were performed on a Agilent Technology 6890N Network GC System equipped with a Agilent 5973 Network Mass Selective Detector and capillary HP-1 column. Purification by gravity column chromatography was carried out by use of Merck Reagents Silica Gel 60 (particle size 0.063-0.200 mm, 70-230 mesh ASTM). Purity of all compounds was >99.5%, as checked by HPLC or GC.

Ultraviolet (UV) spectra were measured on a Hitachi U3300 UV/VIS spectrophotometer. Infrared (IR) spectra were measured on a Jasco FT-IR-5300 Fourier transform infrared spectrometer. The wave numbers reported were referenced to the polystyrene 1601 $cm^{-1}$ absorption. Absorption intensities were recorded by the following abbreviations: s, strong; m, medium; w, weak. The fluorescent intensity was measured on a Hitach F-4500 Florescence Spectrophotometer. Proton NMR spectra were obtained on a Varian Mercury-400 (400 MHz) spectrometer by use of chloroform-d as the solvent and sodium 3-(trimethylsilyl)propionate as internal standard. Carbon-13 NMR spectra were obtained on a Varian Mercury-400 (100 MHz) spectrometer by use of chloroform-d or $D_2O$ as the solvent. Carbon-13 chemical shifts were referenced to the center of the $CDCl_3$ triplet (δ 77.0 ppm). Multiplicities are recorded by the following abbreviations: s, singlet; d, doublet; t, triplet; q, quartet; m, multiplet; J, coupling constant (hertz). Hight-resolution mass spectra were obtained by means of a JEOL JMS-HX110 mass spectrometer. Electrospray ionization mass spectrometry (ESI-MS) analyses were performed on a quadrupole ion trap mass analyzer fitted with an electrospray ionization source of Finnigan LCQ, Finnigan MAT.

Computation was performed on a Silicon Graphics O2+ workstation. The programs Builder and Biopolymer were used for the construction of structures. The program Discover was used for energy minimized with the consistent valence force field (CVFF) until the maximum derivative was less than 1.0 kcal $mol^-Å^{-1}$.

Standard Procedure for the Syntheses of Hydrochloride Salts of NDGA Derivatives. To a solution containing NDGA (1, 1.0 equiv) and potassium carbonate (6.0-10.0 equiv) in acetone was added a nitrogen-containing organic hydrochloride (5.0 equiv). After the solution was heated at reflux for 24 h, it was quenched with water (20 mL). The solution was extracted with ether (3×50 mL) and the combined organic layers were washed with saturated brine, dried over $MgSO_{4(s)}$, filtered, and concentrated under reduced pressure. The residue was purified by column chromatography on silica gel (10% methanol in dichloromethane as eluant) and the desired fraction was concentrated. The resultant was dissolved in acetone (250 mL) and then bubbled with excess $HCl_{(g)}$. The precipitates were dissolved in water and re-precipitated twice by use of acetone at room temperature to give the desired NDGA derivative with purity>99.5%, as checked by HPLC. This procedure was varied as described below for individual NDGA derivatives.

Details of the preparation of specific NDGA derivative compounds according to the present invention will be set forth below in the Examples section.

The present compounds and compositions, in suitable formulations, can be safely administered to a subject in need of such treatment by any effective route known in the art. Such means of administration are known in the art and can be determined by routine experimentation. Examples are intranasal administration; oral administration; inhalation administration; subcutaneous administration; transdermal administration; intradermal administration; intra-arterial administration, with or without occlusion; intracranial administration; intraventricular administration; intravenous administration; buccal administration; intraperitoneal administration; intraocular administration; intramuscular administration; implantation administration; topical administration; and central venous administration. Additionally, the compounds and compositions can be administered as an oral rinse, for example, in a rinse-and-spit treatment one or more times a day.

Moreover, the compounds and compositions can be formulated in liposomal formulations, nanoparticle formulations, or micellar formulations that can be safely administered systemically, such as intravenously, such as by injection into the central vein for example, or intraperitoneally, interstitially, subcutaneously, transdermally, intradermally, intramuscularly, intra-arterially, intra-cranially, or intra-ventricularly.

Furthermore, the compounds and compositions can be formulated in liposomal formulations, nanoparticles formulations, or micellar formulations, or any formulation embedded in a biodegradable polymer, for administration to a subject. Implantation into the brain, for example, can be used for treatment of brain tumors.

The pharmaceutical compositions provided herein are formulated for delivery or administration as described above, for example, in the form of a tablet, a liquid that is either hydrophilic or hydrophobic, a powder such as one resulting from lyophilization, an aerosol, or in the form of an aqueous watersoluble composition, a hydrophobic composition, a liposomal composition, a micellar composition, such as that based on Tween® 80 or diblock copolymers, a nanoparticle composition, a polymer composition, a cyclodextrin complex composition, emulsions, lipid based nanoparticles termed "lipocores." In one preferred embodiment, the pharmaceutical composition comprises one or more compounds of the invention in aqueous solution.

The present invention further features a method of producing the pharmaceutical compositions of the present invention, the method involving making or providing a compound of the invention in a substantially purified form, combining the composition with a pharmaceutically acceptable carrier or excipient, and formulating the composition in a manner that is compatible with the mode of desired administration.

In a further aspect of the present invention, a method of treating a proliferative disease, including pre-malignant, benign or malignant cancer, is provided. Non-limiting examples of cancers and tumors include those of the lung, prostate, breast, colon, liver, kidney, ovarian, cervical, skin, pancreas, brain, nasal, pharyngeal, head, neck, leukemias, lymphomas, gastrointestinal tumor such as stomach and bladder, soft tissue sarcomas and the like, as well as metastases thereof.

The present invention still additionally provides for kits comprising compounds or compositions as above for the treatment of diseases and disorders, in particular viral infections or proliferative diseases such as tumors, wherein the compositions are formulated for delivery as above, including but not limited to intranasal administration, inhalation, oral administration, intravenous administration, intraperitoneal administration and other parenteral administration, or as an oral rinse, or the like. Accordingly, the kits comprise a pharmaceutical composition of the invention in a suitable dosage, and optionally instructions for administration of the composition.

Pharmaceutical compositions provided herein include one or more of the compounds mentioned above and at least one pharmaceutically acceptable carrier or excipient. These compositions may include a buffer, which is selected according to the desired use of the composition, and may also include other substances appropriate for the intended use. Those skilled in the art can readily select an appropriate buffer, a wide variety of which are known in the art, suitable for an intended use. In some instances, the composition can comprise a pharmaceutically acceptable excipient, a variety of which are known in the art. Pharmaceutically acceptable excipients suitable for use herein are described in a variety of publications, including, for example, A. Gennaro (1995 Gennaro, A. (1995). "Remington: The Science and Practice of Pharmacy", 19th edition, Lippincott, Williams, & Wilkins; Ansel, H. C. et al. (1999), Pharmaceutical Dosage Forms and Drug Delivery Systems eds., $7^{th}$ ed., Lippincott, Williams, & Wilkins; Kibbe, A. H. (2000) Handbook of Pharmaceutical Excipients, eds., $3^{rd}$ ed. Amer. Pharmaceutical Assoc.

The compositions herein are formulated in accordance to the mode of potential administration. Thus, if the composition is intended to be administered intranasally or by inhalation, for example, the composition may be converted to a powder or aerosol form, as conventional in the art, for such purposes. Other formulations, such as for oral or parenteral delivery, are also used as conventional in the art.

Compositions for administration herein may form solutions, suspensions, tablets, pills, capsules, sustained release formulations or powders.

Therapeutic Methods

The compounds and compositions of the subject invention find use as therapeutic agents in situations, for example, where one wishes to provide a treatment to a subject who has a proliferative disease such as a malignant, premalignant or benign tumor and where one wishes to provide treatment to viral diseases such as HIV, HPV or HSV.

A variety of animal hosts are treatable according to the subject methods, including human and non-human animals. Generally such hosts are "mammals" or "mammalian," where these terms are used broadly to describe organisms which are within the class mammalia, including the orders carnivore (e.g., dogs and cats), rodentia (e.g., guinea pigs, and rats), and other mammals, including cattle, goats, horses, sheep, rabbits, pigs, and primates (e.g., humans, chimpanzees, and monkeys). In many embodiments, the hosts will be humans. Animal models are of interest for experimental investigations, such as providing a model for treatment of human disease. Further, the present invention is applicable to veterinary care as well.

The compounds and compositions of the present invention can be used to treat a variety of tumors and cancers, including, without limitation, hematological malignancies such as acute lymphoblastic leukemia, acute myeloid leukemia, chronic lymphocytic leukemia, chronic myelogenous leukemia, childhood acute leukaemia, non-Hodgkin's lymphoma, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, adrenocortical carcinoma, anal cancer, astrocytoma, bile duct cancer, bladder cancer, bone cancer osteosarcoma/malignant fibrous histiocytoma, neurological malignancies such as neuroblastoma, glioblastoma, astrocytoma, gliomas, brain stem glioma, brain tumor ependymoma, brain tumor medulloblastoma, neuroblastoma glioblastoma, breast cancer, carcinoid tumor gastrointestinal, carcinoma adrenocortical, carcinoma islet cell, cervical cancer, clear cell sarcoma of tendon sheaths, colon cancer, cutaneous T-cell lymphoma, endometrial cancer, epithelial cancer ovarian, esophageal cancer, Ewing's family of tumors, extragonadal germ cell tumor, extrahepatic bile duct cancer, eye cancer, intraocular melanoma, ductal cancer, eye cancer retinoblastoma, dysplastic oral mucosa, invasive oral tumor, gallbladder cancer, gastric (stomach) cancer, gastrointestinal carcinoid tumor, germ cell tumor extragonadal, germ cell tumor, ovarian tumor, gestational trophoblastic tumor, glioblastoma, glioma, hairy cell leukemia, hepatocellular (liver) cancer, Hodgkin's lymphoma, hypopharyngeal cancer, intraocular melanoma, islet cell carcinoma (endocrine pancreas), Kaposi's sarcoma, laryngeal cancer, leukemia acute lymphoblastic cancer, leukemia acute myeloid cancer, leukemia chronic lymphocytic cancer, leukemia chronic myelogenous cancer, leukemia hairy cell cancer, liver cancer, non-small cell lung cancer, small cell lung cancer, male breast cancer, malignant mesothelioma, medulloblastoma, melanoma, merkel cell carcinoma, multiple endocrine neoplasia syndrome, mycosis fungoides, myeloma multiple, nasal cavity, paranasal and sinus cancer, nasopharyngeal cancer, neuroblastoma, oral cavity and lip cancer, oropharyngeal cancer, osteosarcoma/malignant fibrous histiocytoma of bone, ovarian epithelial cancer, ovarian germ cell tumor, pancreatic cancer, parathyroid cancer, penile cancer, pheochromocytoma, pineal and supratentorial primitive neuroectodermal tumors, pituitary tumor, pleuropulmonary blastoma, prostate cancer, rectal cancer, renal, pelvis and ureter transitional cell cancer, retinoblastoma, rhabdomyosarcoma, salivary gland cancer, sarcoma soft tissue adult, Sezary syndrome, skin cancer, small intestine cancer, stomach (gastric) cancer, testicular cancer, thymoma, thyroid cancer, urethral cancer, transitional and squamous cell urinary carcinoma, gynecological cancer such as cervical cancer ovarian cancer, uterine cancer, endometrial cancer, vaginal cancer, vulvar cancer, Waldenström's macroglobulinemia, and Wilms' tumor, testicular tumors; liver tumors including hepatocellular carcinoma ("HCC") and tumor of the biliary duct; multiple myelomas; tumors of the esophageal tract; other lung tumors including small cell and clear cell; Hodgkin's lymphomas; sarcomas in different organs; as well as those mentioned above; and the like Formulations, Dosages, and Routes of Administration As mentioned above, an effective amount of the active agent is administered to the host, where "effective amount" means a dosage sufficient to produce a desired result. In some embodiments, the desired result is at least a reduction or inhibition of tumor growth as compared to a control.

Typically, the compositions of the instant invention will contain from less than about 1% up to about 99% of the active ingredient, that is, the compounds described herein, preferably with a pharmaceutically acceptable carrier or excipient; optionally, the instant invention will contain about 5% to about 90% of the active ingredient. The appropriate dose to be administered depends on the subject to be treated, such as the general health of the subject, the age of the subject, the state of the disease or condition, the weight of the subject, the size of the tumor, for example. Generally, between about 0.1 mg and about 500 mg or less may be administered to a child and between about 0.1 mg and about 5 grams or less may be administered to an adult. The active agent can be administered in a single or, more typically, multiple doses. Preferred dosages for a given agent are readily determinable by those of skill in the art by a variety of means. Other effective dosages can be readily determined by one of ordinary skill in the art through routine trials establishing dose response curves. The amount of agent will, of course, vary depending upon the particular agent used.

In an alternative embodiment, dosage is defined in terms of the amount of agent delivered to a target tissue (e.g. a tumor, or an organ). In this instance, dosages may be defined as concentrations, e.g. 0.01 µM-10 mM, 0.01 µM-100 mM, etc.

The frequency of administration of the active agent, as with the doses, will be determined by the practitioner based on age, weight, disease status, health status and patient responsiveness. Thus, the agents may be administered one or more times daily, weekly, monthly or as appropriate as conventionally determined. The agents may be administered intermittently, such as for a period of days, weeks or months, then not again until some time has passed, such as 3 or 6 months, and then administered again for a period of days, weeks, or months.

The compounds of the present invention can be incorporated into a variety of formulations for therapeutic administration. More particularly, the compounds can be formulated into pharmaceutical compositions by combination with appropriate, pharmaceutically acceptable carriers or diluents, and may be formulated into preparations in solid, semi-solid, liquid or gaseous forms, such as tablets, capsules, powders, aerosols, liposomes, nanoparticles, granules, ointments, solutions, suppositories, injections, inhalants and aerosols.

As such, administration of the compounds can be achieved in various ways, such as oral, buccal, rectal, intranasal, intravenous, intra-arterial, intra-tracheal, intraventricular, intracranial, interstitial, transdermal, etc., or by inhalation or implantation.

In particular, nanoparticle, micelle and liposomal preparation can be administered systemically, including parenterally and intranasally, as well as interstitially, orally, topically, transdermally, intradermally, via inhalation or implantation, such as for drug targeting, enhancement of drug bioavailability and protection of drug bioactivity and stability. Nanoparticle bound drugs herein are expected to achieve prolonged drug retention in tumors.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. For oral rinses, the preparations can be made in a manner conventional in the art, such as described in, for example, Epstein, J. B. et al. (2002). Fluconazole mouthrinses for oral candidiasis in post-irradiation, transplant, and other patients. Oral Surg. Oral Med. Oral Pathol. Oral Radiol. Endod. 93(6): 671-675. and Pitten, F. et al. (2003) Do cancer patients with chemotherapy-induced leucopenia benefit from an antiseptic chlorhexidine-based oral rinse? A double-blind, block-randomized, controlled study. J. Hosp. Infect. 53(4): 283-291.

Pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents or emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The active agents can be formulated into preparations for injection by dissolving, suspending or emulsifying them in an aqueous or non-aqueous solvent, such as vegetable or other similar oils, including corn oil, castor oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The active agents can be utilized in aerosol formulation to be administered via inhalation. The compounds of the present invention can be formulated into pressurized acceptable propellants such as dichlorodifluoromethane, propane, nitrogen and the like.

Furthermore, the active agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of the present invention compounds calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Kits with multiple or unit doses of the active agent, are included in the present invention. In such kits, in addition to the containers containing the multiple or unit doses of the compositions containing the NDGA derivatives, an informational package insert with instructions describing the use and attendant benefits of the drugs in treating pathological condition of interest may optionally be included.

Preparation of NanoParticles ("NP")

The present invention includes formulations of the compounds of the invention in a NP preparation. A number of different NP formulations suitable for use herein can be made depending on the method of delivery. The NP formulation can differ based on the drug release profile desired, by controlling the molecular weight, the copolymer ratio, the drug loading, the microparticle size and porosity and the fabrication conditions. The NP formulations can also differ on the basis of polymers, stabilizers, and surfactants used in the production process. Different excipients may also have different effects on drug uptake, drug distribution throughout the body and persistence of the drug in plasma. A person having skills conventional in the art will be able to determine the desired properties or characteristics, and accordingly determine the appropriate NP formulation to use.

The polymeric matrix of the NP must meet the criteria of biocompatibility, bioavailability, mechanical strength and ease of processing. The best known polymers for this purpose is the biodegradable poly(lactide-co-glycolide)s ("PLGAs").

NP for use in the pharmaceutical preparations can be made by any process conventional in the art. In one embodiment, the NP can be made as described in, for example, Lockman, P. R., et al. (2002), Nanoparticle Technology for Drug Delivery Across the Blood-Brain Barrier. Drug Development Indus. Pharmacy, 28(1): 1-13. The types of manufacturing process include, for example, emulsion polymerization, interfacial polymerization, desolvation evaporation and solvent deposition.

In the emulsion polymerization process of making the NP herein, the polymerization process consists of building a chain of polymers from a single monomer unit, as described in, for example, Kreuter, J. (1994), Nanoparticles, In Encyclopedia of Pharmaceutical Technology; Swarbick, J.; Boylan, J. C. Eds.; Marcel Dekker (New York, 1994), pp. 165-190. Polymerization occurs spontaneously at room temperature after initiation by either free radical or ion formation, such as by use of high-energy radiation, UV light, or hydroxyl ions. Once polymerization is complete the solution is filtered and neutralized. The polymers form micelles and droplets consisting of from about 100 to $10^7$ polymer molecules. Surfactants and stabilizers are generally not need in this process. This process can also be accomplished in an organic phase rather than an aqueous phase.

The NP herein can also be made by an interfacial polymerization process as described in, for example, Khouri, A. I., et al. (1986), Development of a new process for the manufacture of polyisobutyl-cyanoacrylate nanoparticles, Int. J. Pharm., 28: 125. In this process, monomers are used to create the polymer and polymerization occurs when an aqueous and organic phase are brought together by homogenization, emulsification, or micro-fluidization under high-torque mechanical stirring. For example, polyalkylcyanoacrylate nanocapsules containing the catecholic butanes, such as the NDGA compounds of this invention, can be made by combining the lipophilic NDGA compounds and the monomer in an organic phase, dissolving the combination in oil, and slowly adding the mixture through a small tube to an aqueous phase with constant stirring. The monomer can then spontaneously form 200-300 nm capsules by anionic polymerization. A variation of this process involves adding a solvent mixture of benzyl benzoate, acetone, and phospholipids to the organic phase containing the monomer and the drug, as described in, for example, Fessi, H., et al. (1989). Nanocapsule formulation by interfacial deposition following solvent displacement. Int. J. Pharm., 55: R1-R4. This creates a formulation in which the drug is encapsulated and protected against degradation until it reaches the target tissue.

Macromolecules such as albumin and gelatin can be used in oil denaturation and desolvation processes in the production of NPs. In the oil emulsion denaturation process, large macromolecules are trapped in an organic phase by homogenization. Once trapped, the macromolecule is slowly introduced to an aqueous phase undergoing constant stirring. The nanoparticles formed by the introduction of the two immiscible phases can then be hardened by crosslinking, such as with an aldehyde or by heat denaturation.

Alternatively, macromolecules can form NPs by "desolvation." In the desolvation process, macromolecules are dissolved in a solvent in which the macromolecules reside in a swollen, coiled configuration. The swollen macromolecule is then induced to coil tightly by changing the environment, such as pH, charge, or by use of a desolvating agent such as ethanol. The macromolecule may then be fixed and hardened by crosslinking to an aldehyde. The NDGA compounds can be adsorbed or bound to the macromolecule before crosslinking such that the derivatives become entrapped in the newly formed particle.

Solid lipid NP can be created by high-pressure homogenization. Solid lipid NPs have the advantage that they can be sterilized and autoclaved and possess a solid matrix that provides a controlled release.

The present invention further includes NP with different methods of drug loading. The NP can be solid colloidal NP with homogeneous dispersion of the drug therein. The NP can be solid NP with the drug associated on the exterior of the NP, such as by adsorption. The NP can be a nanocapsule with the drug entrapped therein. The NP can further be solid colloidal NP with homogeneous dispersion of the drug therein together with a cell surface ligand for targeting delivery to the appropriate tissue.

The size of the NPs may be relevant to their effectiveness for a given mode of delivery. The NPs typically ranges from about 10 nm to about 1000 nm; optionally, the NPs can range from about 30 to about 800 nm; further typically, from about 60 to about 270 nm; even further typically, from about 80 to about 260 nm; or from about 90 to about 230 nm, or from about 100 to about 195. Several factors influence the size of the NPs, all of which can be adjusted by a person of ordinary skill in the art, such as, for example, pH of the solution used during polymerization, amount of initiation triggers (such as heat or radiation, etc.) and the concentration of the monomer unit. Sizing of the NPs can be performed by photon correlation spectroscopy using light scattering.

The NPs herein, such as polysaccharide NPs or albumin NPs, may optionally be coated with a lipid coating. For example, polysaccharide NPs can be crosslinked with phosphate (anionic) and quaternary ammonium (cationic) ligands, with or without a lipid bilayer, such as one containing dipalmitoyl phosphatidyl choline and cholesterol coating. Other polymer/stabilizer include, but is not limited to: soybean oil; maltodextrin; polybutylcyanoacrylate; butylcayanoacrylate/dextran 70 kDa, Polysorbate-85; polybutylcyanoacrylate/dextran 70 kDa, polysorbate-85; stearic acid; poly-methylmethylacrylate.

The NP preparations containing the compounds of the invention, such as by adsorption to the NPs, can be administered intravenously for treatment of tumors, for example, in the brain, heart and reticuloendothelial cell ("RES") containing organs, such as liver, spleen and bone marrow. To avoid undesirable uptake of these NP preparations by the reticuloendothelial cells, the NPs may be coated with a surfactant or manufactured with a magnetically responsive material.

Thus, optionally, a surfactant may be used in conjunction with the NP. For example, polybutylcyanoacrylate NPs can be used with a dextran-70,000 stabilizer and Polysorbate-80 as a surfactant. Other surfactants include, but not limited to: Polysorbate-20, 40, or 60; Poloxamer 188; lipid coating-dipalmitoyl phosphatidylcholine; Epikuron 200; Poloxamer 338; Polaxamine 908; Polaxamer 407. For example, Polyaxamine 908 may be used as a surfactant to decrease uptake of NPs into the RES of the liver, spleen, lungs, and bone marrow.

The magnetically responsive material can be magnetite ($Fe_3O_4$) which can be incorporated into the composition for making the NP. These magnetically responsive NPs can be externally guided by a magnet.

In another embodiment, the NPs herein can be made as described in Mu, L. and Feng, S. S. (2003) (A novel controlled release formulation for the anticancer drug paclitaxel (Taxol®): PLGA nanoparticles containing vitamin E TPGS. J. Control. Rel. 86: 33-48), using a blend of poly(lactide-co-glycolide)s ("PLGAs") and d-α-tocopheryl polyethylene glycol 1000 succinate (vitamin E TPGS or TPGS). The latter can also act as an emulsifier, in addition to being a matrix material.

Preparation of Micelle Forming Carriers

The present invention includes the disclosed NDGA derivatives, formulated in micelle forming carriers, where the micelles are produced by processes conventional in the art. Examples of such are described in, for example, Liggins, R. T. and Burt, H. M. (2002) Polyether-polyester diblock copolymers for the preparation of paclitaxel loaded polymeric micelle formulations. Adv. Drug Del. Rev. 54: 191-202; Zhang, X. et al. (1996) Development of amphiphilic diblock copolymers as micellar carriers of taxol., Int. J. Pharm. 132: 195-206; and Churchill, J. R., and Hutchinson, F. G. (1988). Biodegradable amphipathic copolymers. U.S. Pat. No. 4,745, 160. In one such method, polyether-polyester block copolymers, which are amphipathic polymers having hydrophilic (polyether) and hydrophobic (polyester) segments, are used as micelle forming carriers.

Another type of micelles is, for example, that formed by the AB-type block copolymers having both hydrophilic and hydrophobic segments, which are known to form micellar structures in aqueous media due to their amphiphilic character, as described in, for example, Tuzar, Z. and Kratochvil, P. (1976). Block and graft copolymer micelles in solution. Adv. Colloid Interface Sci. 6:201-232; and Wilhelm, M. et al. (1991). Poly(styrene-ethylene oxide) block copolymer micelle formation in water: a fluorescence probe study. Macromolecules 24: 1033-1040. These polymeric micelles are able to maintain satisfactory aqueous stability irrespective of the high content of hydrophobic drug incorporated within the micelle inner core. These micelles, in the range of approximately <200 nm in size, are effective in reducing non-selective RES scavenging and shows enhanced permeability and retention at solid tumor sites. This characteristic allows for the accumulation of anti-cancer drug, such as the NDGA derivatives, to accumulate at the cancer site.

Further, for example, poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hr, or a temperature as high as 190° C. can be used if the reaction is carried out for only about 2 hr.

In one embodiment, N-isopropylacrylamide ("IPAAm") (Kohjin, Tokyo, Japan) and dimethylacrylamide ("DMAAm") (Wako Pure Chemicals, Tokyo, Japan) can be used to make hydroxyl-terminated poly(IPAAm-co-DMAAm) in a radical polymerization process, using the method of Kohori, F., et al. (1998). Preparation and characterization of thermally responsive block copolymer micelles comprising poly(N-isopropylacrylamide-b-D,L-lactide). J. Control. Rel. 55: 87-98. The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori, F., et al. (1999). Control of adriamycin cytotoxic activity using thermally responsive polymeric micelles composed of poly(N-isopropylacrylamide-co-N,N-dimethylacrylamide)-b-poly(D,L-lactide). Colloids Surfaces B: Biointerfaces 16: 195-205.

The compounds of the invention can be loaded into the inner cores of micelles and the micelles prepared simultaneously by a dialysis method. For example, a chloride salt of an NDGA derivative can be dissolved in N,N-dimethylacetamide ("DMAC") and added by triethylamine ("TEA"). The poly(IPAAm-co-DMAAm)-b-poly(D,L-lactide) block copolymer can be dissolved in DMAC, and distilled water can be added. The solution of NDGA derivative and the block copolymer solution can be mixed at room temperature, followed by dialysis against distilled water using a dialysis membrane with 12,000-14,000 molecular weight cut-off (Spectra/Por®2, spectrum Medical Indus., CA. U.S.A.) at 25° C. Poly(IPAAm-co-DMAAm)-b-poly(D,L-lactide) micelles incorporating derivatives can be purified by filtration with a 20 nm pore sized microfiltration membrane (ANODISC™, Whatman International), as described in Kohori, F., et al. (1999).

Preparation of Multivesicular Liposomes Containing NDGA Compounds

Multivesicular liposomes ("MVL") can be produced by any method conventional in the art, such as, for example, the double emulsification process as described in Mantriprgada, S. (2002) A lipid based depot (DepoFoam®) technology) for sustained release drug delivery. Prog Lipid Res. 41: 392-406.

Formulation for Oral Delivery

The compounds of Scheme 1 are water-soluble, hydrophilic compounds, and can be readily formulated for oral delivery. Compounds of Scheme 2 are hydrophobic and can be formulated in suitable lipophilic solvents known in the art. The compounds can be formulated with a pharmaceutically acceptable carrier or excipient and delivery of such as oral formulations, such as in the form of an aqueous liquid solution of the compound, or the compounds can be lyophilized and delivered as a powder, or made into a tablet, or the compounds can be encapsulated. Tablets can be enteric coated tablets, with formulations for sustained release, either slow release or rapid release formulations. Various other carriers, excipients and adjuvants could be used as are well known to those skilled in pharmaceutical preparations. The amount of the compounds to be included in the oral formulations can be adjusted depending on the desired dose to be administered to a subject. Such an adjustment is within the skill of persons conventional in the art.

Intra-Arterial Administration

The present invention includes formulation of the compounds for intra-arterial administration as is conventional in the art, as described in, for example, Doolittle, N. D. et al. (2000) Cancer 88(3): 637-647 and Cloughesy, T. F. et al. (1997) J. Neurononcol. 35: 121-131, with or without accompanying blood brain barrier disruption ("BBBD"), and with or without occlusion, such as in hepatic artery chemoemobolization, as described in Drougas, J. G. et al. (1998) Hepatic artery chemoembolization for management of patients with advanced metastatic carcinoid tumors. Am. J. Surg. 175: 408-412 and Desai, D. C. et al. (2001) Serum pancreastatin levels predict response to hepatic artery chemoembolization and somatostatin analogue therapy in metastatic neuroendocrine tumors. Reg Peptides 96: 113-117. Briefly, where compounds of the invention are administered intra-arterially with occlusion, primary arteries leading to the target site are catheterized and the compounds are administered through a catheter. Embolization of the arteries, in order to retain the compounds at the target site for a longer period, is performed using polyvinyl alcohol particles alone or in combination with coils. Intra-arterial delivery of the compounds is limited to water soluble compositions, and accordingly, the compounds disclosed herein will be advantageous for such delivery. The drugs or agents herein can be dissolved in saline prior to intra-arterial injection and such injection may be preceded by heparin treatment and sedation. For safest treatment of brain tumor, preferably, intra-arterial administration is conducted before tumor burden becomes excessive.

Osmotic disruption of the blood brain barrier ("BBB") as conventional in the art may accompany intra-arterial delivery of the agents herein as described in, for example, Doolittle, N. D. et al. (2000); Sato, S. et al., Acta Neurochir (Wien) 140: 1135-1141; disc 1141-1132 (1998); and Bhattacharjee, A. K. et al. Brain Res Protocol 8: 126-131 (2001). Such a procedure can be used to increase the transfer of drugs into the central nervous system ("CNS") preferably just prior to intra-arterial delivery. For such disruption, a catheter is placed into an artery, usually the superficial temporal artery, leading to the brain and the BBB is disrupted with a solution of mannitol. This invasive procedure is typically performed while the patient is under general anesthesia. Such treatment may require prior hydration and administration of anticonvulsants and/or atropine.

Formulation of NDGA Compounds for Intranasal Delivery

The present invention includes formulations of the compounds of the invention, for intranasal delivery and intranasal delivery. Intranasal delivery may advantageously build up a higher concentration of the active agents in the brain than can be achieved by intravenous administration. Also, this mode of delivery avoids the problem of first pass metabolism in the liver and gut of the subject receiving the drug.

The amount of the active agent that can be absorbed partly depends on the solubility of the drug in the mucus, a composition that consists of about 95% water solution of serum proteins, glycoproteins, lipids and electrolytes. Generally, as lipophilicity of the active agents herein increases, the drug concentration in the CSF also increases. See, for example, Minn, A. et al. (2002). Drug transport into the mammalian brain: the nasal pathway and its specific metabolic barrier. J. Drug Target, 10: 285-296.

The compounds can be dissolved in a pharmaceutically acceptable carrier such as saline, phosphate buffer, or phosphate buffered saline. In one embodiment, a 0.05 M phosphate buffer at pH 7.4 can be used as the carrier, as described in, for example, Kao, H. D., et al. (2000). Enhancement of the Systemic and CNS Specific Delivery of L-Dopa by the Nasal Administration of Its Water Soluble Prodrugs, Pharmaceut. Res., 17(8): 978-984.

Intranasal delivery of the present compounds may be optimized by adjusting the position of the subject when administering the agents. For example, the head of the patient may be variously positioned upright-90°, supine-90°, supine-45°, or supine-70°, to obtain maximal effect.

The carrier included in the present compositions may be any material that is pharmaceutically acceptable and compatible with the active agents of the composition. Where the carrier is a liquid, it can be hypotonic or isotonic with nasal fluids and within the pH of about 4.5 to about 7.5. Where the carrier is in powdered form it is also within an acceptable pH range.

The carrier composition for intranasal delivery may optionally contain lipophilic substances that may enhance absorption of the active agents across the nasal membrane and into the brain via the olfactory neural pathway. Examples of such lipophilic substances include, but are not limited to, gangliosides and phosphatidylserine. One or several lipophilic adjuvants may be included in the composition, such as, in the form of micelles.

The pharmaceutical composition of active agents for intranasal delivery to a subject for treatment of tumor and other proliferative diseases, disorders, or conditions herein can be formulated in the manner conventional in the art as described in, for example, U.S. Pat. No. 6,180,603. For example, the composition herein can be formulated as a powder, granules, solution, aerosol, drops, nanoparticles, or liposomes. In addition to the active agents, the composition may contain appropriate adjuvants, buffers, preservatives, salts. Solutions such as nose drops may contain anti-oxidants, buffers, and the like.

Delivery by Implantation

The disclosed compounds and compositions, may be delivered to a subject for treatment by surgical implantation into a tumor site, with or without surgical excision of the tumor, such as by implantation of a biodegradable polymer containing the compounds. In one embodiment, this method of treatment can be performed, for example, after surgical resection, such as in the treatment and resection of brain tumor, as described in, Fleming, A. B. and Saltzman, W. M., Pharmacokinetics of the Carmustine Implant, Clin. Pharmacokinet, 41: 403-419 (2002). This method of delivery is applicable to not only brain tumors but to other tumors as well. This treatment may be combined with other conventional therapy besides or in addition to surgery, such as radiotherapy, chemotherapy or immunotherapy.

Thus, the biodegradable polymer herein can be any polymer or copolymer that would dissolve in the interstitial fluid, without any toxicity or adverse effect on host tissues. Preferably, the polymer or monomers from which the polymer is synthesized is approved by the Food and Drug Administration for administration into humans. A copolymer having monomers of different dissolution properties is preferred so as to control the dynamics of degradation, such as increasing the proportion of one monomer over the other to control rate of dissolution.

In one embodiment, the polymer is a copolymer of 1,3-bis-(p-carboxyphenoxy)propane and sebacic acid [p(CPP:SA)], as described in Fleming A. B. and Saltzman, W. M., Pharmacokinetics of the Carmustine Implant, Clin. Pharmacokinet, 41: 403-419 (2002); and Brem, H., and Gabikian, P. (2001). Biodegradable polymer implants to treat brain tumors. J. Control. Rel. 74: 63-67. In another embodiment, the polymer is a copolymer of polyethylene glycol ("PEG") and sebacic acid, as described in Fu, J. et al. (2002). New Polymeric Carriers for Controlled Drug Delivery Following Inhalation or Injection. Biomaterials, 23: 4425-4433.

Polymer delivery systems are also applicable to delivery of compounds disclosed herein. The compounds are combined with the biodegradable polymers and surgically implanted at the tumor site. Some polymer compositions are also usable for intravenous or inhalation therapy herein.

Delivery Through Inhalation

The compounds disclosed herein may be delivered systemically and/or locally by administration to the lungs through inhalation. Inhalation delivery of drugs has been well accepted as a method of achieving high drug concentration in the pulmonary tissues without triggering substantial systemic toxicity, as well as a method of accomplishing systemic circulation of the drug. The techniques for producing such formulations are conventional in the art.

For pulmonary delivery via inhalation, the compounds herein may be formulated into dry powders, aqueous solutions, liposomes, nanoparticles, or polymers and administered, for example, as aerosols. Hydrophilic formulations may also be taken up through the alveolar surfaces and into the bloodstream for systemic applications.

In one embodiment, the polymers containing the disclosed compounds are made and used as described in Fu, J. et al. (2002). For example, the polymers herein can be polymers of sebacic acid and polyethylene glycol ("PEG"), or can be poly(lactic-co-glycolic) acid ("PLGA"), or polymers of polyethyleneimine ("PEI") and poly-L-lysine ("PLL").

In another embodiment, the compounds for inhalation delivery may be dissolved in saline or ethanol before nebulization and administered, as described in Choi, W. S. et al. (2001). Inhalation delivery of proteins from ethanol suspensions. Proc. Natl. Acad. Sci. USA, 98(20): 11103-11107.

In a further embodiment, the compounds herein are also effective when delivered as a dry powder, prepared in the manner conventional in the art, as described in, for example, Patton, J. S. et al., Inhaled Insulin, Adv. Drug Deliv. Rev., 35: 235-247 (1999).

The present invention includes delivery of the compounds with the aid of microprocessors embedded into drug delivery devices, such as, for example, SmartMist™ and AERx™, as described in, for example, Gonda, I., et al. (1998). Inhalation delivery systems with compliance and disease management capabilities. J. Control. Rel. 53: 269-274.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in greater detail with reference to the following specific, non-limiting examples.

EXAMPLES

Example 1 meso-2,3-Dimethyl-1,4-bis(3,4-[2-(pyrrolidino) ethoxyphenyl])butane Tetrakishydrochloride Salt (5a)

The Standard Procedure (above) was carried out using NDGA (1, 1.43 g, 4.73 mmol, 1.0 equiv), potassium carbonate (6.53 g, 47.3 mmol, 10.0 equiv), acetone (150 mL) and 1-(2-chloroethyl)pyrrolidine hydrochloride (4.03 g, 23.7 mmol, 5.0 equiv) to give pure 5a (2.45 g, 3.54 mmol) as yellow gum in 75% yield: $^1$H NMR (CDCl$_3$, 400 MHz) δ 0.77 (d, J=6.4 Hz, 6H, 2×CH$_3$), 1.68 (m, 2H, 2×CH), 1.74-1.77 (m, 16H, 8×pyrrolidine CH$_2$), 2.20 (dd, J=13.6, 9.6 Hz, 2H, 2×ArCH), 2.61-2.66 (m, 16H, 8×pyrrolidine NCH$_2$), 2.72-2.75 (m, 2H, 2×ArCH), 2.88 (t, J=12.2 Hz, 8H, 4×CH$_2$N), 4.08 (t, J=5.6 Hz, 8H, 4×CH$_2$O), 6.61-6.63 (m, 4H, 4×ArH), 6.76 (d, J=8.4 Hz, 2H, 2×ArH); $^{13}$C NMR (CDCl$_3$, 100 MHz) δ 16.01, 23.42, 38.83, 39.39, 53.36, 54.63, 54.92, 68.16, 68.27, 113.86, 114.99, 121.45, 134.98, 146.78, 148.49; IR KBr 3429 (s), 2959 (m), 2709 (m), 1635 (w), 1515 (m), 1457 (m), 1263 (s), 1229 (m), 1141 (s), 1018 (m) cm$^{-1}$; MS (FAB) m/e (relative intensity) 691 (M+, 41), 594 (7), 592 (6), 523 (3), 496 (3), 399 (12), 220 (4), 98 (100), 84 (81), 56 (8); HRMS (FAB) calcd for C$_{42}$H$_{66}$N$_4$O$_4$ 690.5084. found 691.5088.

Example 2 meso-2,3-Dimethyl-1,4-bis(3,4-[2-(piperidino)ethoxyphenyl])butane Tetrakishydrochloride Salt (5b)

In order to make this compound, the non-salt base compound of the compound referred to herein as P$_4$N, the Standard Procedure (above) was carried out using NDGA (1, 1.11 g, 3.67 mmol, 1.0 equiv), potassium carbonate (5.07 g, 36.72 mmol, 10.0 equiv), acetone (150 mL) and 1-(2-chloroethyl) piperidine monohydrochloride (3.38 g, 18.35 mmol, 5.0 equiv) to give pure 5b (1.93 g, 2.46 mmol) as white solids in 67% yield: $^1$H NMR (CDCl$_3$, 400 MHz) δ 0.78 (d, J=6.4 Hz, 6H, 2×CH$_3$), 1.38-1.45 (m, 8H, 4×piperidine CH$_2$), 1.42-2.58 (m, 16H, 8×piperidine CH$_2$), 1.55-1.68 (m, 2H, 2×CH), 2.36-2.51 (m, 16H, 8×piperidine CH$_2$N), 2.64 (dd, J=13.2, 1.2 Hz, 2H, 2×ArCH), 2.71 (t, J=6.0 Hz, 8H, 4×CH$_2$N), 4.03 (t, J=2.4 Hz, 8H, 4×CH$_2$O), 6.75 (d, J=7.9 Hz, 2H, 2×ArH), 6.63 (s, 2H, 2×ArH), 6.75 (dd, J=7.9, 1.6 Hz, 2H, 2×ArH); $^{13}$C NMR (CDCl$_3$, 100 MHz) δ 15.95, 24.00, 25.82, 38.82, 39.21, 54.81, 54.87, 57.81, 67.03, 67.18, 113.80, 114.90, 121.28, 134.78, 146.69, 148.41; IR KBr 3429 (s), 2951 (m), 2687 (m), 1633 (w), 1515 (m), 1455 (m), 1262 (s), 1140 (s), 1017 (m) cm$^{-1}$; MS (FAB) m/e (relative intensity) 747 (M+, 63), 636 (8), 634 (4), 524 (3), 413 (5), 374 (4), 346 (3), 241 (6), 128 (5), 112 (100), 98 (63), 84 (15), 56 (7); HRMS (FAB) calcd for C$_{46}$H$_{74}$N$_4$O$_4$ 746.5710. found 747.5713.

Unless otherwise indicated herein, "P$_4$N" refers to the HCl salt of this compound.

Example 3 meso-2,3-Dimethyl-1,4-bis(3,4-[2-(morpholino) ethoxyphenyl])butane Tetrakishydrochloride Salt (5c)

The Standard Procedure (above) was carried out using NDGA (1, 1.19 g, 3.94 mmol, 1.0 equiv), potassium carbonate (5.43 g, 39.36 mmol, 10.0 equiv), acetone (150 mL), and 4-(2-chloroethyl)morpholine hydrochloride (3.67 g, 19.7 mmol, 5.0 equiv) to give pure 5c (2.46 g, 3.26 mmol) as white solids in 83% yield: $^1$H NMR (CDCl$_3$, 400 MHz) δ 0.72 (d, J=6.4 Hz, 6H, 2×CH$_3$), 1.62-1.68 (m, 2H, 2×CH), 2.16 (dd, J=13.4, 9.2 Hz, 2H, 2×ArCH), 2.72 (dd, J=13.2, 4.6 Hz, 2H, 2×ArCH), 2.41-2.59 (m, 16H, 8×morpholine CH$_2$), 2.70 (t, J=12.2 Hz, 8H, 4×CH$_2$N), 3.46-3.72 (m, 16H, 8×morpholine CH$_2$), 4.01 (t, J=5.6 Hz, 8H, 4×CH$_2$O), 6.57-6.58 (m, 4H, 4×ArH), 6.72 (d, J=8.4 Hz, 2H, 2×ArH); $^{13}$C NMR (CDCl$_3$, 100 MHz) δ 15.88, 38.51, 39.03, 53.21, 53.79, 57.41, 59.82, 66.46, 66.56, 66.69, 113.65, 114.70, 121.36, 134.84, 146.41, 148.14; IR KBr 3419 (s), 2956 (m), 2606 (m), 1635 (w), 1515 (m), 1456 (m), 1264 (s), 1139 (s), 1104 (m), 1041 (m), 917 (w) cm$^{-1}$; MS (FAB) m/e (relative intensity) 755 (M+, 3), 263 (2), 236 (3), 149 (8), 114 (100), 100 (67), 56 (18), 42 (10); HRMS (FAB) calcd for C$_{42}$H$_{66}$N$_4$O$_8$ 754.4881. found 755.4885.

Example 4 meso-2,3-Dimethyl-1,4-bis(3,4-[3-(morpholino)propoxyphenyl])butane Tetrakishydrochloride Salt (5d)

The Standard Procedure (above) was carried out using NDGA (1, 1.69 g, 5.59 mmol, 1.0 equiv), potassium carbonate (4.63 g, 33.5 mmol, 6.0 equiv), acetone (50 mL), and 4-(3-chloropropyl)morpholine hydrochloride (4.55 g, 27.9 mmol, 5.0 equiv) to give pure 5d (3.70 g, 3.88 mmol) as white solids in 69% yield: $^1$H NMR (D$_2$O, 400 MHz) δ 0.80 (d, J=6.4 Hz, 6H, 2×CH$_3$), 1.73-1.77 (m, 2H, 2×CH), 2.24-2.38 (m, 8H, 4×CH$_2$), 2.33 (dd, J=13.6, 9.6 Hz, 2H, 2×ArCH), 2.74 (dd, J=13.6, 5.2 Hz, 2H, 2×ArCH), 3.19 (t, J=12.4 Hz, 8H, 4×CH$_2$N), 3.35-4.12 (m, 32H, 16×morpholine CH$_2$), 4.18 (t, J=5.2 Hz, 8H, 4×CH$_2$O), 6.84 (dd, J=8.0, 1.6 Hz, 2H, 2×ArH), 6.92 (d, J=1.6 Hz, 2H, 2×ArH), 7.02 (d, J=8.0 Hz, 2H, 2×ArH); $^{13}$C NMR (CDCl$_3$, 100 MHz) δ 16.63, 24.26, 39.02, 39.87, 52.73, 55.52, 64.73, 66.93, 67.26, 115.26, 116.11, 123.33, 137.43, 146.41, 148.19; IR (KBr) 3441 (s), 2934 (s), 2870 (m), 2607 (m), 2474 (m), 1642 (w), 1510 (m), 1425 (m), 1220 (s), 1159 (m), 1107 (s), 985 (m), 896 (w) cm$^{-1}$; MS (FAB) m/e (relative intensity) 811 (M+, 40), 684 (10), 557 (3), 406 (100), 343 (8), 271 (39), 203 (3), 128 (8); HRMS (FAB) calcd for C$_{46}$H$_{74}$N$_4$O$_4$, 810.5506. found 810.5491.

Example 5 meso-2,3-Dimethyl-1,4-bis[3,4-(phenyl piperidine-1-carboxylate)]butane (6a)

To a solution of NDGA (1, 453 mg, 1.49 mmol, 1.0 equiv) in pyridine (20 mL) stirred at 0° C. was added 1-piperidinecarbonyl chloride (1.32 g, 8.94 mmol, 6.0 equiv). After the reaction mixture was stirred at room temperature for 24 h, it was quenched with water and the remaining pyridine was removed under reduced pressure. The resultant was extracted with $CH_2Cl_2$ (3×50 mL) and the combined organic layers were washed with saturated brine, dried over $CaCl_{2(s)}$, filtered, and concentrated under reduced pressure. The residue was purified by use of column chromatography (50% EtOAc in hexane as eluant) to give 6a (797 mg, 1.07 mmol) in 72% yield as white solids with purity>99.5% as checked by GC: mp (recrystallized from EtOAc) 171.5-172.4° C.; TLC $R_f$ 10.51 (50% EtOAc in hexane as eluant); $^1H$ NMR ($CDCl_3$, 400 MHz) δ 0.81 (d, J=6.4 Hz, 6H, 2×$CH_3$), 1.58-1.68 (m, 24H, 12×$CH_2$), 1.72-1.78 (m, 2H, 2×CH), 2.27 (dd, J=13.2, 10.2 Hz, 2H, 2×ArCH), 2.76 (dd, J=13.6, 3.6 Hz, 2H, 2×ArCH), 3.49-3.56 (m, 16H, 8×$CH_2$N), 6.95 (dd, J=8.2, 2.0 Hz, 2H, 2×ArH), 7.02 (s, 2H, 2×ArH), 7.08 (d, J=8.2 Hz, 2H, 2×ArH); $^{13}C$ NMR ($CDCl_3$, 100 MHz) δ 16.00, 24.14, 24.31, 25.90, 39.03, 39.73, 45.12, 45.46, 122.94, 123.86, 126.32, 139.71, 141.15, 142.86, 152.93, 153.02; IR (KBr) 3425 (m), 2933 (s), 2858 (m), 1729 (s), 1509 (m), 1418 (s), 1376 (w), 1351 (w), 1251 (s), 1235 (s), 1197 (s), 1139 (s), 1118 (s), 1048 (w), 1023 (m), 894 (w), 852 (w), 794 (w), 749 (w) $cm^{-1}$; MS (EI) m/e (relative intensity) 747 (M+, 5), 702 (2), 674(1), 635 (6), 575(17), 505 (18), 373 (5), 112 (100), 84 (3), 69 (20); HRMS (EI) calcd for $C_{42}H_{58}N_4O_8$, 746.4255. found 746.4253.

Example 6 meso-2,3-Dimethyl-1,4-bis[3,4-(methyl phenyl carbonate)]butane (6b)

To a solution of NDGA (1, 1.07 g, 3.53 mmol, 1.0 equiv) in pyridine (50 mL) at 0° C. was added methyl chloroformate (3.33 g, 35.27 mmol, 10.0 equiv). After the reaction mixture was stirred at room temperature for 24 h, it was quenched with water and pyridine was removed under reduced pressure. The resultant was extracted with $CH_2Cl_2$ (3×50 mL) and the combined organic layers were washed with saturated brine, dried over $CaCl_2$ $_{(s)}$, filtered, and concentrated under reduced pressure. The residue was purified by column chromatography on silica gel (50% EtOAc in hexane as eluant) to give 6b (1.57 g, 2.93 mmol) in 83% yield as white solids with purity>99.5% as checked by GC: mp (recrystallized from EtOAc) 101.6-102.4° C.; TLC $R_f$0.63 (50% EtOAc in hexane as eluant); $^1H$ NMR ($CDCl_3$, 400 MHz) δ 0.83 (d, J=6.4 Hz, 6H, 2×$CH_3$), 1.76-1.78 (m, 2H, 2×CH), 2.32 (dd, J=13.2, 9.2 Hz, 2H, 2×ArCH), 2.76 (dd, J=13.2, 4.6 Hz, 2H, 2×ArCH), 3.90 (s, 6H, 2×$CH_3$O), 3.91 (s, 6H, 2×$CH_3$O), 6.99-7.03 (m, 4H, 4×ArH), 7.16 (d, J=8.4 Hz, 2H, 2×ArH); $^{13}C$ NMR ($CDCl_3$, 100 MHz) δ 16.31, 39.03, 39.52, 55.91, 122.84, 123.63, 127.53, 140.55, 141.09, 142.23, 153.67; IR (KBr) 2971 (m), 2915 (w), 1772 (s), 1508 (m), 1446 (m), 1379 (w), 1197 (s), 1131 (m), 1048 (m), 931 (m), 824 (w), 810 (w), 783 (w) $cm^{-1}$; MS (EI) m/e (relative intensity) 534 (M+, 13), 490 (9), 459 (5), 400 (4), 195 (100), 151 (70), 137 (19), 105 (13), 91 (7), 77 (9); HRMS (EI) calcd for $C_{26}H_{30}O_{12}$, 534.1737. found 534.1739.

Example 7 meso-2,3-Dimethyl-1,4-bis(benzo[d][1,3]dioxol-2-one)butane (7)

To a solution of NDGA (1, 1.26 g, 4.15 mmol, 1.0 equiv) in THF (50 mL) at room temperature was added 1,1'-carbonyldiimidazole (2.69 g, 16.61 mmol, 4.0 equiv). After the reaction mixture was stirred at room temperature for 24 h, it was quenched with water and THF was removed under reduced pressure. The resultant was extracted with $CH_2Cl_2$ (3×50 mL) and the combined organic layers were washed with saturated brine, dried over $CaCl_{2(s)}$, filtered, and concentrated under reduced pressure. The residue was purified by column chromatography on silica gel (20% EtOAc in hexane as eluant) to give 7 (1.11 g, 3.13 mmol) in 74% yield as white solids with purity>99.5% as checked by GC: mp (recrystallized from EtOAc) 172.6-173.4° C.; TLC $R_f$ 0.59 (20% EtOAc in hexane as eluant); $^1H$ NMR ($CDCl_3$, 400 MHz) δ 0.83 (d, J=6.8 Hz, 6H, 2×$CH_3$), 1.72-1.78 (m, 2H, 2×CH), 2.37 (dd, J=13.2, 9.6 Hz, 2H, 2×ArCH), 2.76 (dd, J=13.6, 4.4 Hz, 2H, 2×ArCH), 6.97 (dd, J=8.2, 1.2 Hz, 2H, 2×ArH), 7.02 (s, 2H, 2×ArH), 7.13 (d, J=8.2 Hz, 2H, 2×ArH); $^{13}C$ NMR ($CDCl_3$, 100 MHz) δ 16.18, 39.64, 39.93, 110.17, 110.90, 125.34, 139.25, 141.68, 143.60, 151.59; IR (KBr) 2991 (s), 1821 (s), 1638 (w), 1488 (m), 1438 (m), 1384 (m), 1347 (m), 1322 (w), 1239 (s), 1152 (m), 1044 (m), 965 (s), 931 (m), 882 (w), 832 (w), 786 (w), 757 (m), 711 (w) $cm^{-1}$; MS (EI) m/e (relative intensity) 354 (M+, 24), 298 (1), 205 (36), 189 (6), 163 (24), 149 (100), 105 (37), 91 (8), 77 (32), 65 (5), 51 (9); HRMS calcd for $C_{20}H_{18}O_6$, 354.1103. found 354.1108.

Example 8

The Secreted Alkaline Phosphatase (SeAP) Assay

The screening of the new NDGA derivatives for inhibition of Tat transactivation was achieved with SeAP assay originally described by Berger et al.[12,13,19] The COS cells were maintained in Iscove's Modified Dulbecco's Medium supplemented with 10% (v/v) fetal serum, 100 unit/mL penicillin, 0.25 µg/mL Fungizone, and 100 µg/mL streptomycin. The medium used for dilution of compounds and maintenance of cultures during the assay was the same as described above. Cultures were maintained in disposable tissue culture labware at 37° C. in a humidified atmosphere of $CO_2$ (5.0%) in air. Compounds were dissolved as stock solutions in water or dimethyl sulfoxide (DMSO) at the concentration of 10 mM. The stock solutions were diluted with $H_2O$ (5a-d) or DMSO (6a,b and 7) and dilute by medium to the desired concentration by a 30-s vortex just before addition into the cell culture. Triplicate cell samples were seeded at density of ~1.5×10⁴ cell per well in Libro 24-well flat-bottom culture dishes (17-mm diameter), which were incubated for 24 h until they reached 50% confluence. The cells were cotransfected by the calcium phosphate procedure with DNA from plasmids pBC12/CMV/t2 (coding for Tat function, 0.20 µg/well) and pBC12/HIV/SeAP (0.40 µg/well). Cells and DNAs were kept in contact for 6.0 h; then the medium was aspirated and replaced by 500₁ of medium containing the test compound. The compound-treated cells were then incubated for additional 48 h. At the end of incubation, an aliquot of cell culture medium was removed and SeAP activities were analyzed by spectrametric method.[20] The sample of culture medium were heated at 65° C. for 5.0 min to inactivate endogenous phosphatases selectively (SeAP is thermal stable). The buffer solution of 2×SeAP (100 µL, 1.0 M diethanolamine, pH 9.8; 0.50 mM $MgCl_2$; 10 mM L-homoarginine) was added to the culture medium sample (100 µL) in a 96-well flat-bottom culture dish (Corning). Then, the substrate solution (20 mL, 120 mM, p-nitrophenyl phosphate dissolved in 1×SeAP buffer) was dispensed into each well containing the reaction mixture. The absorbance at wavelength 405 nm specific for the hydrolysis product was read at 2.5 min intervals at 37° C. over the course of 60 min on an EL340i microplate reader (Bio-tek Instruments) with 5 s automatic shaking before each reading. The percent inhibition of SeAP expression was calculated at 60 min.[12,13] This assay was used in Example 11, below.

Example 9

Cytotoxicity Assay

The cytotoxicity of $P_4N$ against Vero cells and human cancer cells HEP3B, HT29 and MCF7 was analyzed using an MTT [3-(4,5-dimethylthiazol-2-yl)-2,5-diphenyltetrazolium bromide]-based assay (Sigma). The absorbance of $OD_{570}$ was a measurement of formazon crystals solubilized in DMSO from metabolically active cells. Procedures were discussed in Huang R C C, et al. in Antiviral Res 58, 57-64 2003.[10]

Example 10

Figure 2:
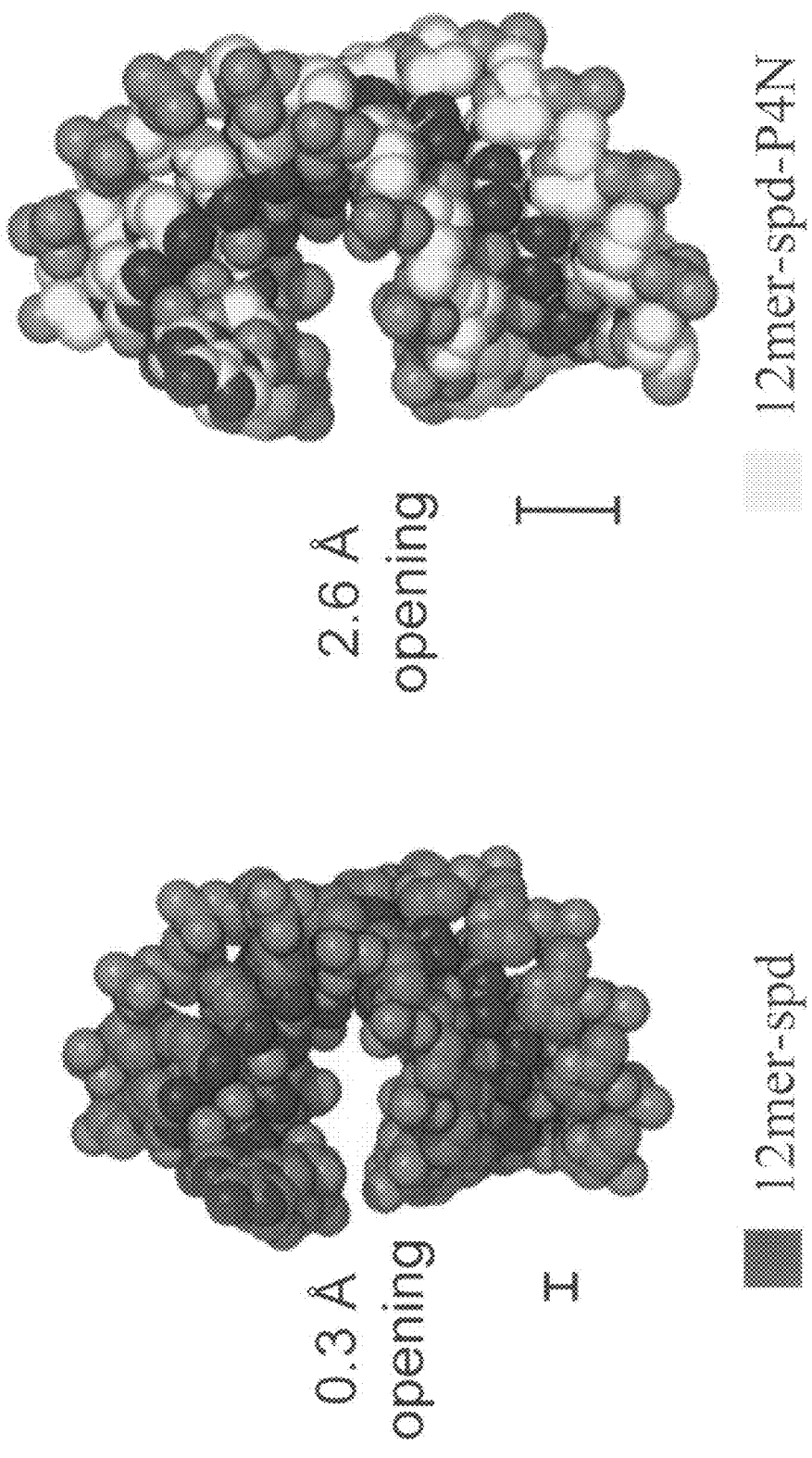
FIG. 2: Major groove of DNA widens in the presence of $P_4N$. Space filling representations of the crystal structure of a 12mer crystallized with Spermidine (12mer-spd, with carbon atoms colored green) and of a 12mer, dsOLIGOsp (dGGGGCGGGG with two or three additional base-pairs on either the 5' or 3' ends) crystallized in the presence of spermidine and $P_4N$ (12mer-spd-$P_4N$, with carbon atoms colored yellow) illustrating the widening of the major groove of DNA in the presence of $P_4N$ (Ref. 25, JMB 349, 731-744 2005).

Interaction of $P_4N$ with Double Stranded Deoxy Oligonucleotide Containing Sp1 Binding Site We have shown in crystallographic studies that the presence of the drug $P_4N$ alters the conformation of $dsOLIGO_{sp}$ by the opening of the major groove and exposure of the minor groove, two features of the structure of the DNA that are critical for the binding of Sp1. These structural changes in the grooves of the DNA are attributed to the $P_4N$-induced changes in the global conformation of the DNA (FIG. 2).[21] The opening or widening of the groove alters the conformation of the $dsOLIGO_{sp}$, thereby inhibiting or preventing the binding of Sp1. Accordingly, $P_4N$ and the other compounds of the invention should be useful for treating diseases and disorders wherein Sp1 binding involved in the disease process (e.g. in viral replication or tumor growth).

Figure 3:
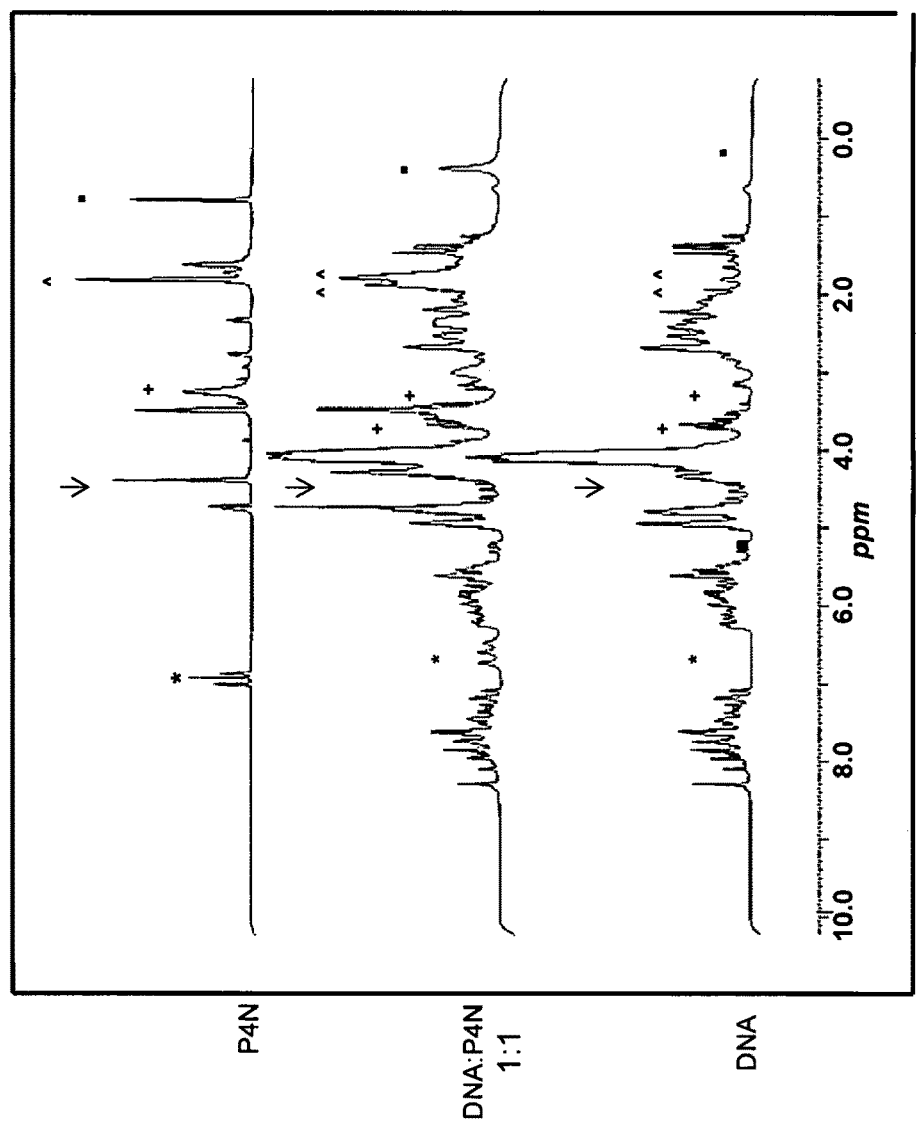
FIG. 3: 1D 1H NMR spectra of free DNA, free P4N and 1:1 molar ratio DNA:P4N. The resonances with the largest chemical shift perturbation are indicated
dsOLIGOsp. 5'GATGGGCGGGACG3'
3'CTACCCGCCCTGC5
Figure 4:
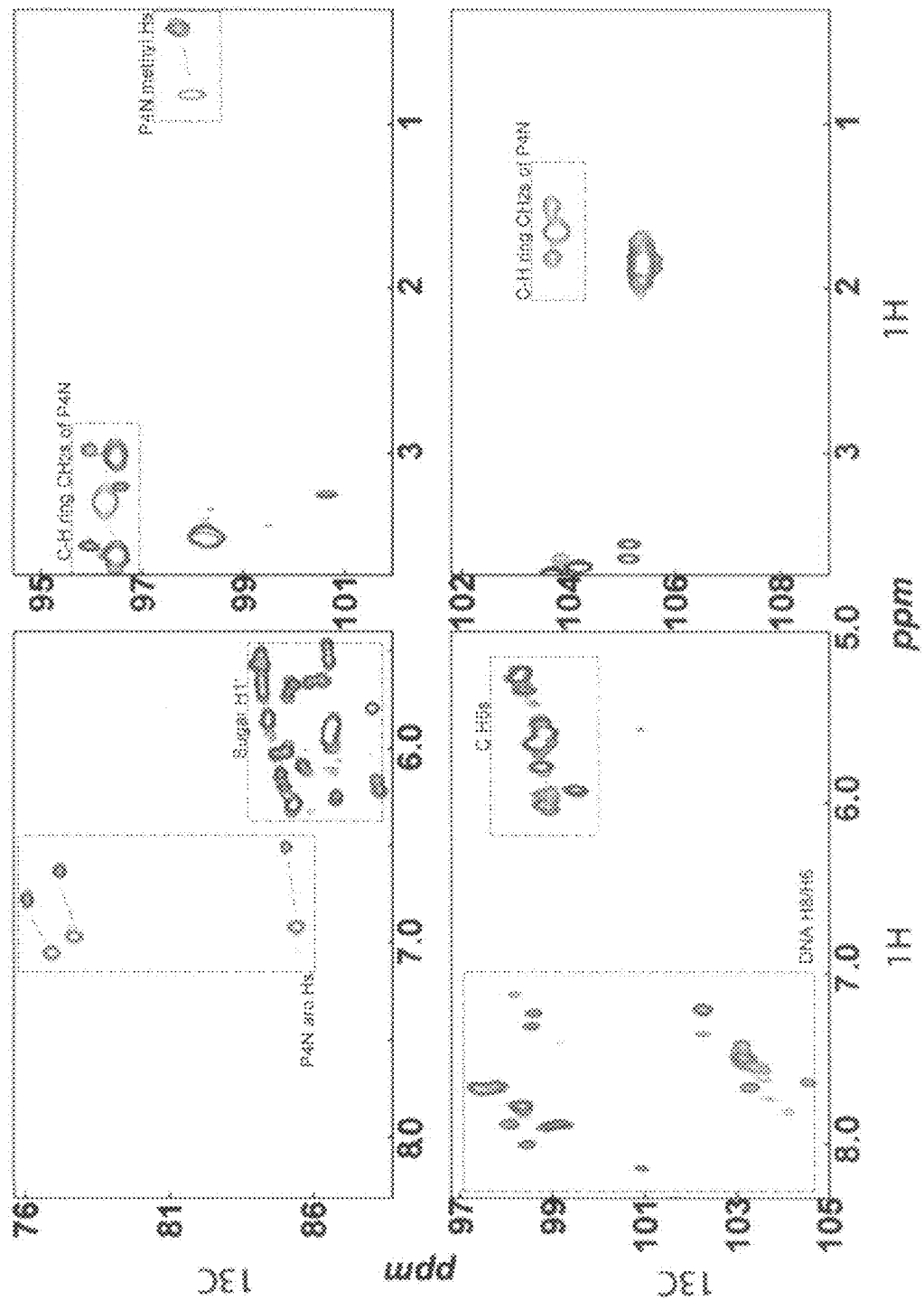
FIG. 4: Superposition of representative region of the 2D 1H-13C HSQC spectra of the free DNA (green) free P4N (red) and 1:1 complex (blue). The spectra were collected with folding in 13C dimension for improved resolution.
Figure 5:
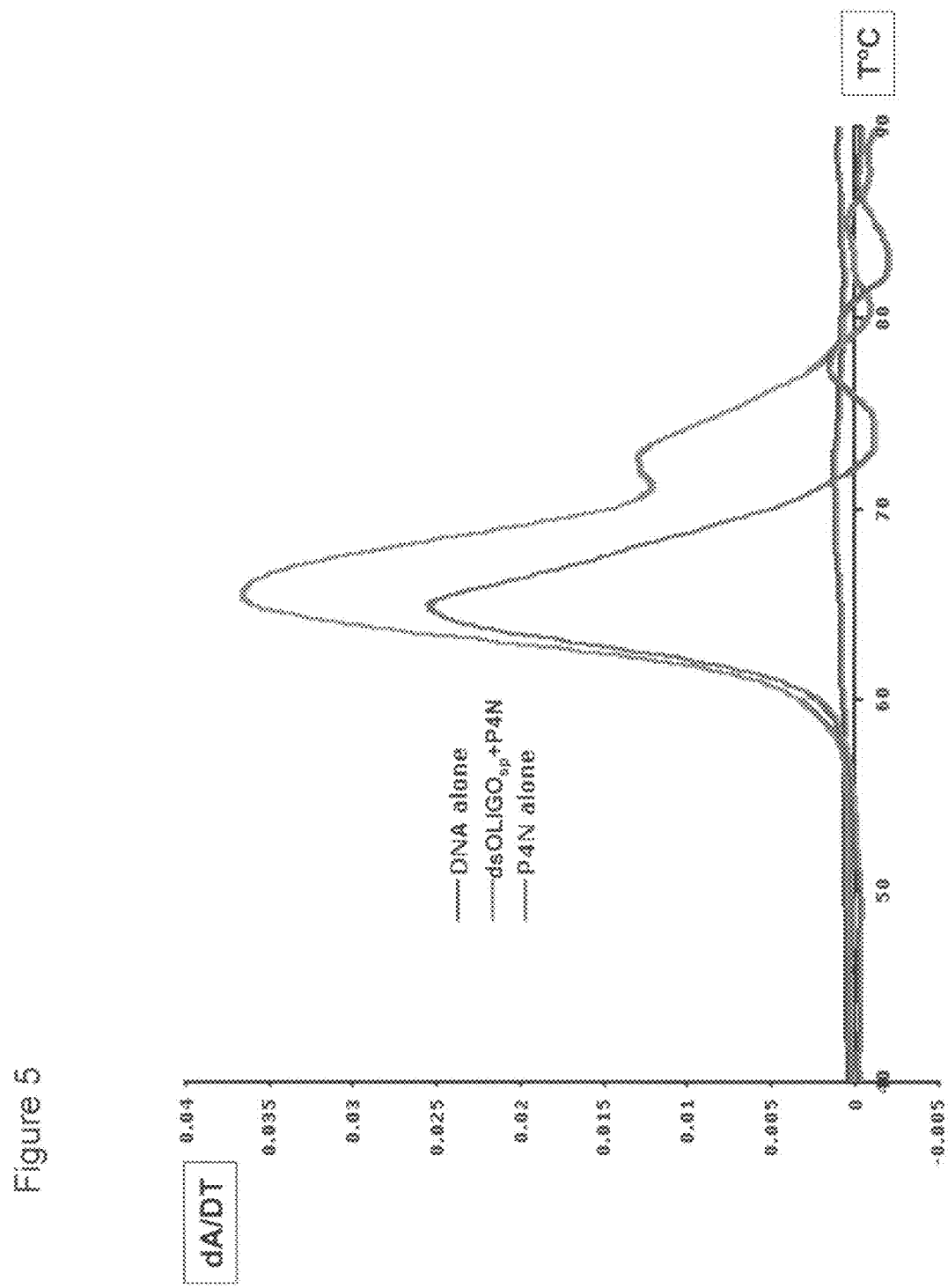
FIG. 5: First derivate (dA/DT) of the absorbance (A) with respect to Temperature (T) as a function of temperature.
Figure 6:
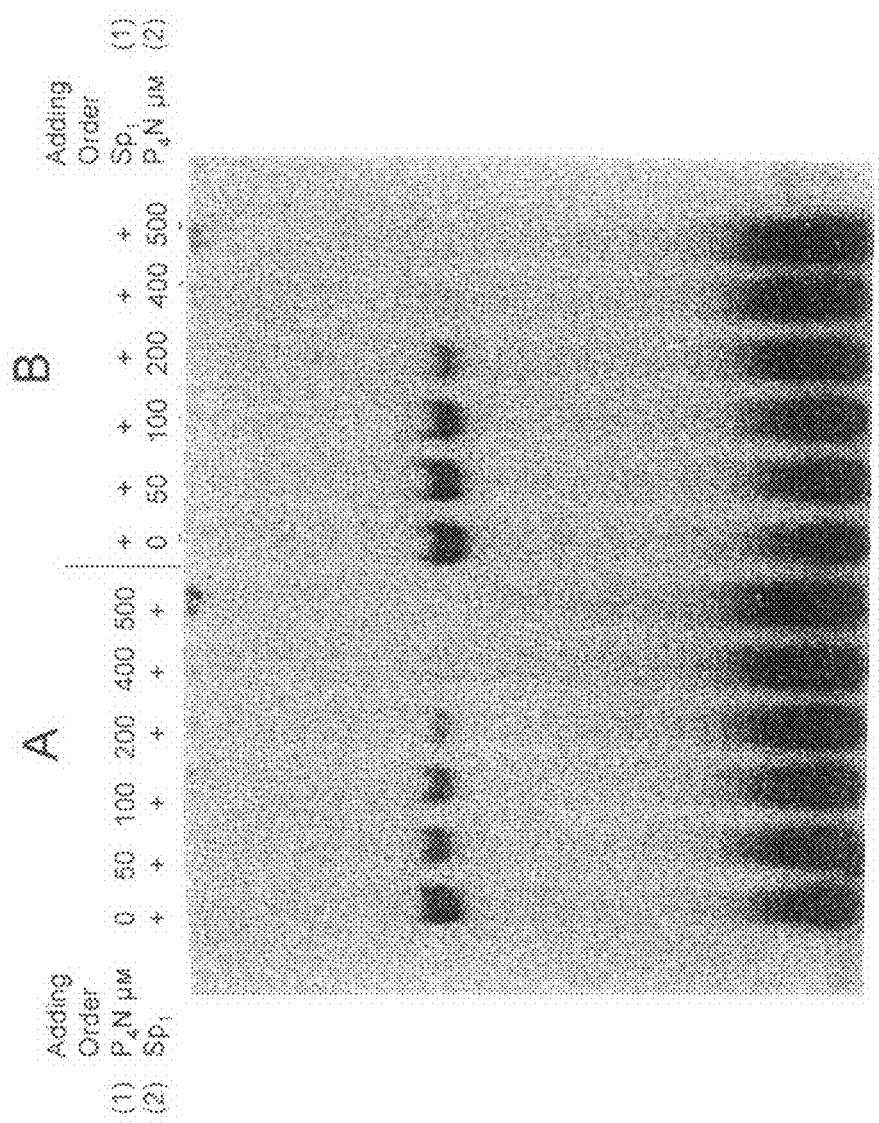
FIG. 6: Electrophoretic Mobility-Shift Analysis of Interaction of HIVLTR (−87 to −49) with Sp1 Protein in the presence and absence of competitor $P_4N$. Blocking the Sp1 binding to (A) and replacement of the bound Sp1 from (B). HIVLTR (−87 to −49) by $P_4N$: 2 ng $^{32}$P-labeled HIVLTR, was incubated with $P_4N$ (0, 50, 100, 200, 400, 800 μM) for 30 minutes. Reaction was continued for additional 30 minutes in the presence of 2 ng of recombinant Sp1-167 C(A). 2 ng of $^{32}$P-labeled HIVLTR was incubated with 2 ng of recombinant Sp1-167 C for 30 minutes. Reaction was continued for additional 30 minutes in the presence of a series of concentrations of $P_4N$(HCl salt) (0, 50, 100, 200, 400, 800 μM) (B). (Reference 10.)

The titration of the Sp1 cognate binding site with $P_4N$ was further studied by 1D $^1H$ NMR (FIG. 3). The drug binds to the DNA in the micro-molar range. Changes in the chemical shifts and the line-widths of both the DNA and the drug indicate structural perturbations of the DNA upon titration with $P_4N$. The 2D $^1H$-13C HSQC data (FIG. 4) are consistent with $P_4N$ adopting two different conformations and/or exhibiting two different modes of binding. This is reflected in the split of the well resolved resonances of the carbon-nitrogen ring $CH_2$ protons (which lie in an area of the spectrum that is free of DNA peaks). As shown on both FIG. 3 and FIG. 4 the largest perturbations of the $P_4N$ chemical shifts induced upon binding are those of the $CH_3$ protons, aromatic protons and the carbon-nitrogen ring $CH_2$ protons. The NMR results are consistent (or in agreement) with the results from the UV-melts which unequivocally demonstrate that $P_4N$ binds to its Sp1 cognate binding site with the formation of at least two distinct complexes (FIG. 5). Binding of Sp1 to $dsOLIGO_{sp}$ and binding of $P_4N$ to $dsOLIGO_{sp}$ are both reversible as shown in a competitive band-shift analysis (FIG. 6).

Figure 7:
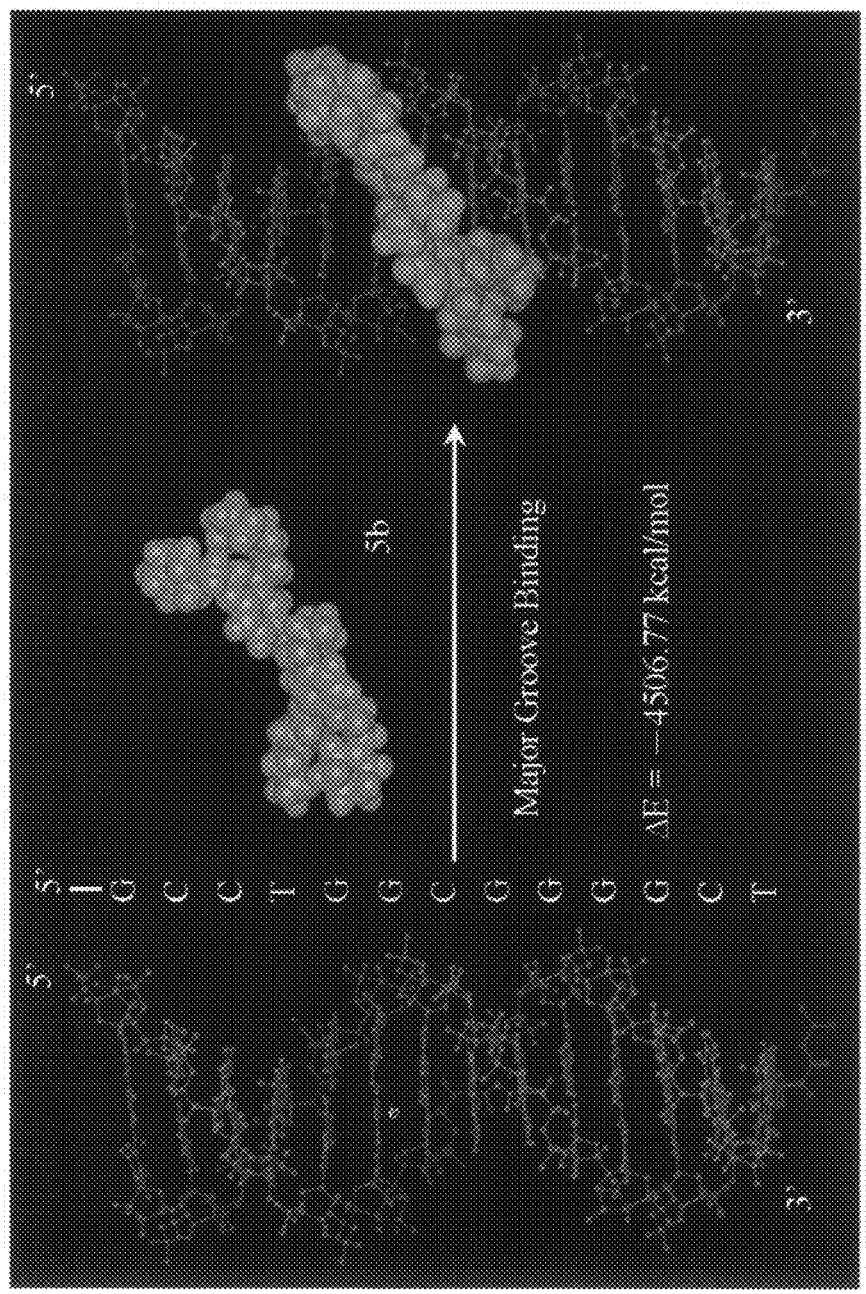
FIG. 7: Consistent Valence Forcefilled (EVFF) Calculations of $P_4N$ in the Major Groove of dsOLIGOMERsp.

We have also performed graphic molecular modeling of $P_4N$ with $dsOLIGO_{sp}$ using the programs "Builder and Biopolymer for Construction of Structures". The energies for conformations were minimized by the use of the program "Discover with the Consistent Valence Forcefield (CVFF). Compound 5b, $P_4N$ binds the major groove of the Sp1 cognate binding site with a $\Delta E$ of −4506.77 KCal/Mole. $P_4N$ on the other hand, was found to be expelled from the minor groove of the $dsOLIGO_{sp}$ because of steric congestion (FIG. 7).

Example 11

Inhibition of HIV Tat-Regulated Transactivation by NDGA Derivatives

Figure 8:
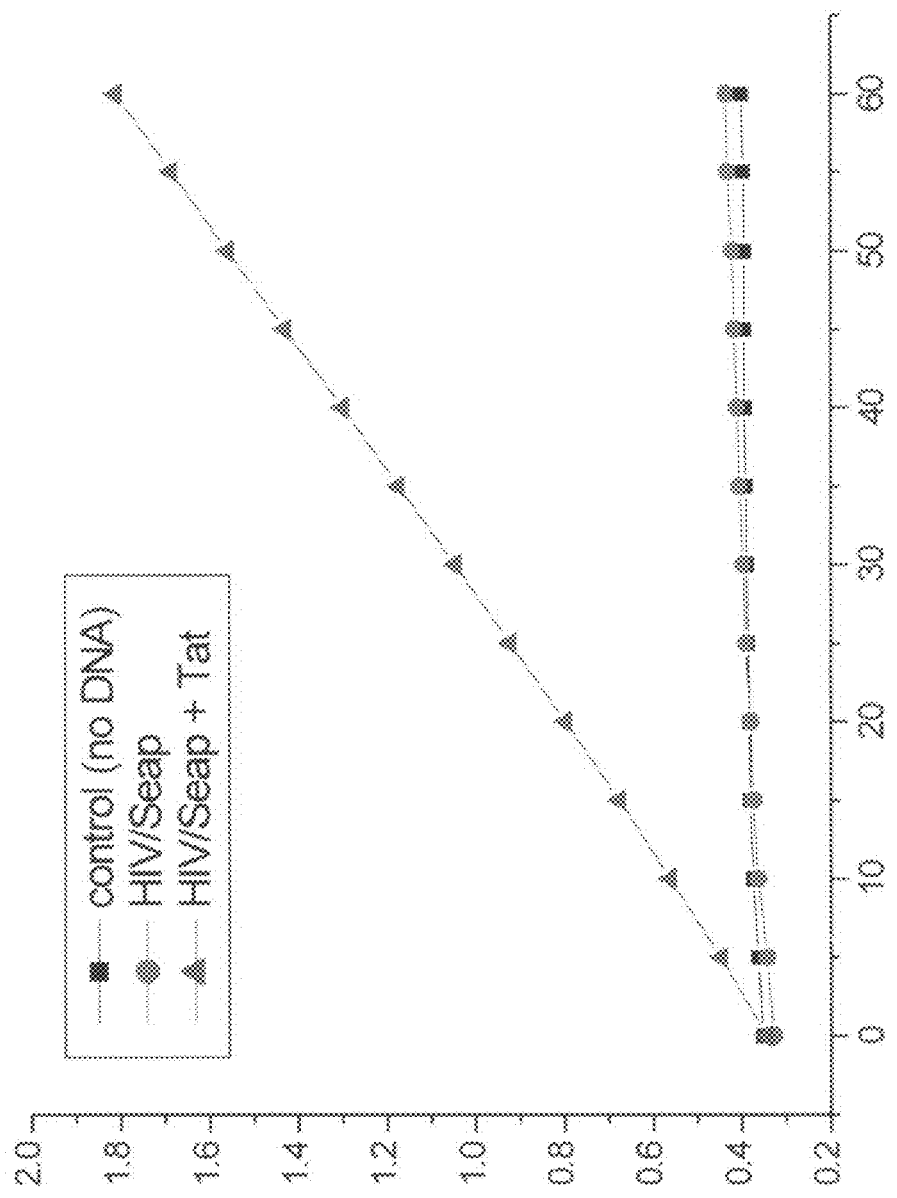
FIG. 8: Tat Induced HIV Transactivation. SeAP standard assay for secreted alkaline phosphatase (Reference 21) Induction of HIVLTR promoter activity by HIV Tat (Reference 12). SeAP level ($A_{405}$) is plotted against time (minutes).

Two plasmid constructs[19] were used to test the effect of synthesized NDGA derivatives on Tat-regulated HIV transactivation as described previously.[12,13,19] The plasmid constructs included a cytomegalovirus (CMV) promoter driven tat gene and SP1 regulated HIV LTR promoter driven reporter gene (i.e., SeAP). A standard SeAP assay in the absence of drug was initially run to find out efficiency of transfection. Results, shown in FIG. 8, indicate a nearly 5 fold increment in Tat-induced SeAP expression after 60 min in comparison with the control levels of the enzyme activity (i.e. without DNA transfection or transfection with HIV/SeAP alone). Both of them were close to the baseline.

Figure 9:
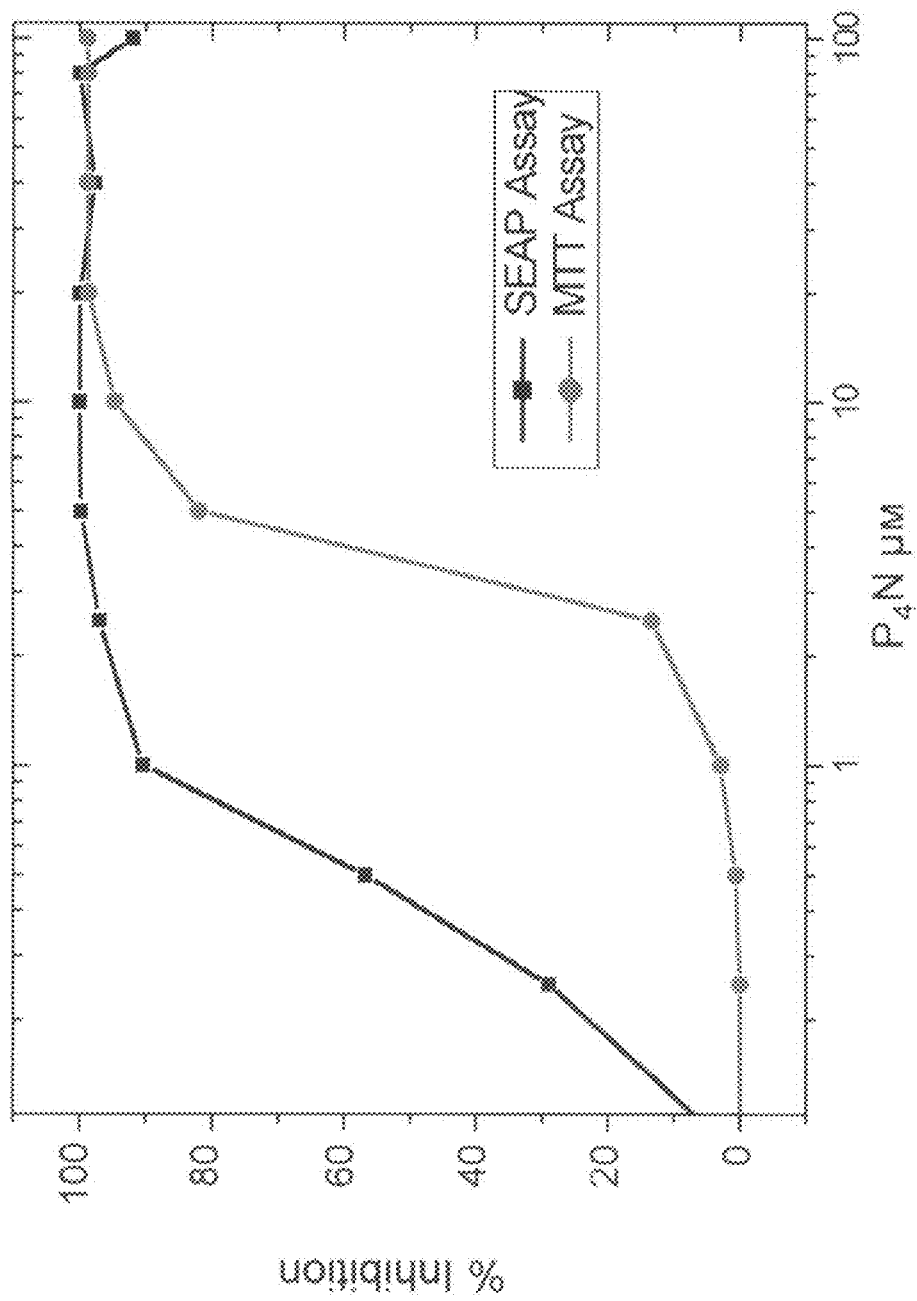
FIG. 9: Inhibition of HIV Tat-Regulated transactivation by Compound 5b $P_4N$. The COS cells were co-transfected with a Tat-producing plasmid and a plasmid containing the HIV LTR linked to the SeAP reporter gene. Transfected cells were treated with various concentrations of 5b $P_4N$. After 48 h, aliquots of media were removed and analysis of SeAP activity was performed. The percent inhibition of SeAP activity by 5b $P_4N$ (—■—) was calculated in comparison with the percent of growth inhibition of untransfected COS cells by $P_4N$ (—●—)

We tested the NDGA derivatives 5a-d, 6a,b, and 7 with the SeAP assay, of which the results displayed a dose-dependent inhibitory activity of Tat transactivation (see Table 1). At 80 μM, all of these NDGA derivatives inhibited the Tat-regulated SeAP production to the level>90% and exhibited a greater inhibitory activity than the parent NDGA (1, $IC_{50}$=20 μM) and Mal.4 (3, $IC_{50}$=25 μM).[12] Except 5a ($IC_{50}$17.2 μM) and 5c ($IC_{50}$ 17.3 μM), all other NDGA derivatives of these new series also showed greater potency than $M_4N$ (2, $IC_{50}$=11.1 μM).[9] $P_4N$ showed no effect on the growth of the cos cells ≦1 μM, yet at this concentration HIV transactivation was fully inhibited (FIG. 9). In fact, $P_4N$ is the strongest antiviral and anticancer inhibitor of all of the NDGA derivatives that we have developed to date.

TABLE 1

Inhibition (%) of HIV Tat-regulated Transactivation in COS Cells by NDGA derivatives.

| Compound | Concentration (μM)[a] | | | | | | | | | | | $IC_{50}$[b] (μM) |
|---|---|---|---|---|---|---|---|---|---|---|---|---|
| | 0.10 | 0.25 | 0.50 | 1.0 | 2.5 | 5.0 | 10 | 20 | 40 | 80 | 100 | |
| 5a | 18.1 | 15.4 | 27.2 | 19.6 | 31.0 | 14.1 | 26.3 | 59.1 | 94.8 | 97.1 | 100 | 17.23 |
| 5b | 8.7 | 4.3 | 29.0 | 56.8 | 90.6 | 97.0 | 99.8 | 100 | 100 | 100 | 97.7 | 0.88 |
| 5c | 5.0 | 16.5 | 9.9 | 8.1 | 4.6 | 13.3 | 25.4 | 58.9 | 86.0 | 96.8 | 100 | 17.34 |
| 5d | 15.0 | 15.9 | 10.6 | 9.5 | 52.7 | 89.5 | 96.0 | 99.9 | 99.8 | 100 | 89.5 | 2.41 |
| 6a | 0 | 3.5 | 5.8 | 11.7 | 46.2 | 78.6 | 84.0 | 86.1 | 83.8 | 90.1 | 89.8 | 2.79 |

TABLE 1-continued

Inhibition (%) of HIV Tat-regulated Transactivation in COS Cells by NDGA derivatives.

| Compound | \multicolumn{11}{c}{Concentration (μM)[a]} | $IC_{50}$[b] (μM) |
|---|---|---|---|---|---|---|---|---|---|---|---|---|
|  | 0.10 | 0.25 | 0.50 | 1.0 | 2.5 | 5.0 | 10 | 20 | 40 | 80 | 100 |  |
| 6b | 9.8 | 12.3 | 16.0 | 13.1 | 15.1 | 38.0 | 51.6 | 58.4 | 70.8 | 93.4 | 88.9 | 9.41 |
| 7 | 7.5 | 18.1 | 4.2 | 5.9 | 23.7 | 47.1 | 51.2 | 68.8 | 85.7 | 96.3 | 91.6 | 8.54 |

[a]All data represent the average of three experiments.
[b]Concentrations exhibiting 50% inhibitory ($IC_{50}$) represented the mean of the triplicate determinations with standard deviations.

Example 12

$P_4N$ as Anti-HSV Agent in a Mouse Vaginal Model

Figure 10:
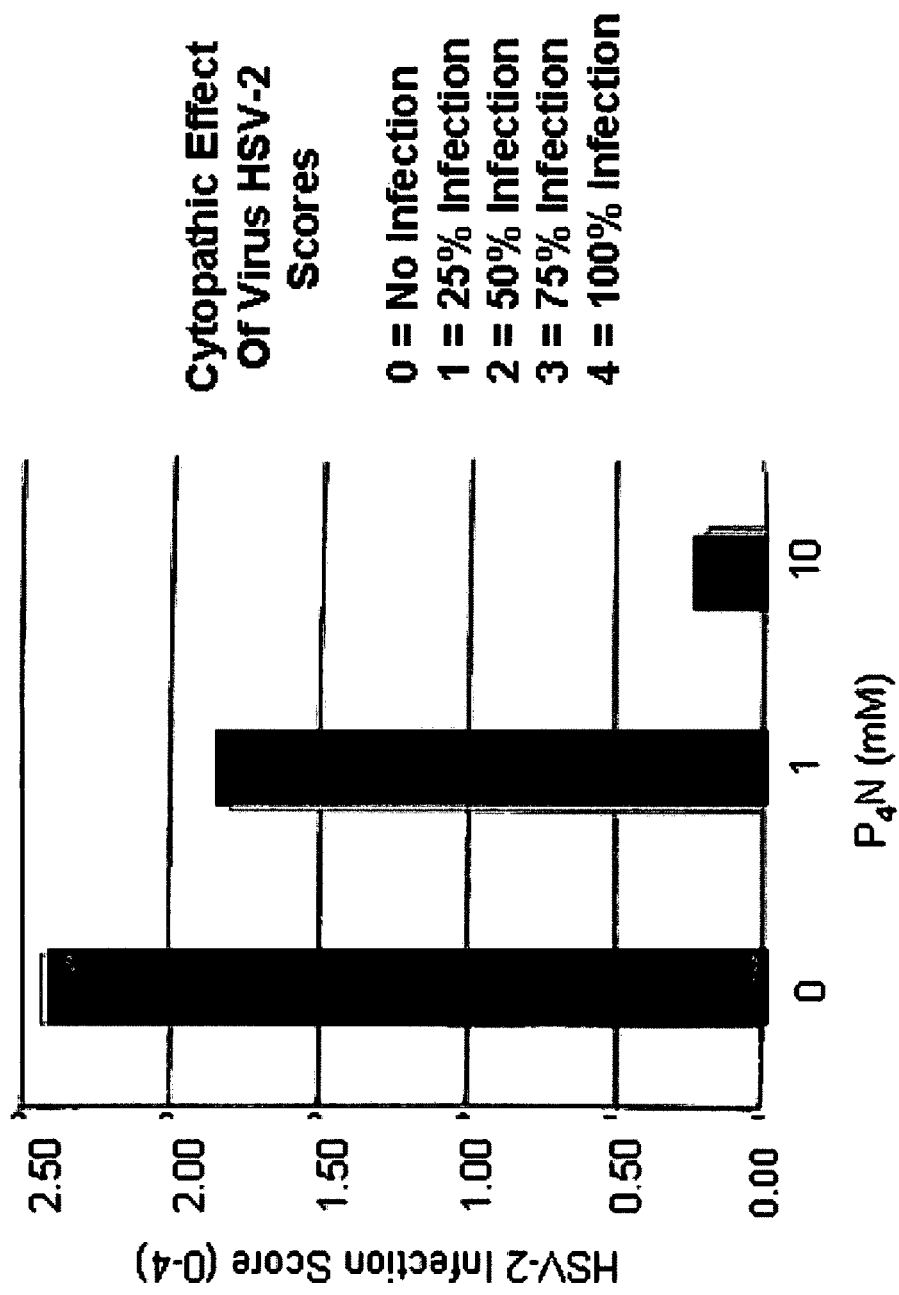
FIG. 10: Efficacy of $P_4N$ Against HSV-2 in a Mouse Vaginal Model

The efficacies of $P_4N$ against HSV-2 in a mouse vaginal model system have been examined. Progestin treated female CF-1 mice (10 per group) were infected with HSV-2 in the absence or presence of $P_4N$ (in PBS). At the end of three days, the vaginal lavages were collected from the washings of the vaginal regions. The status of the vaginal HSV-2 infection and replication were examined by their cytopathic effects on cultured human foreskin fibroblast cells. Monitoring and scoring were carried out by three persons independently. $P_4N$ was found to be quite effective. At 10 mM concentration only 2 of 10 mice were weakly infected. An average scale of 0.19 was obtained with little or no toxicity in animals as compared to an average 2.43 scale when viral infection was proceeded in the absence of $P_4N$ (FIG. 10).

Example 13

$P_4N$ Inhibits the Growth of Human Tumor Cells in Culture

We have previously shown that $M_4N$ arrests tumor cells growth at $G_2$-M phase of the cell cycle by reducing the level of $Cdc_2$ protein and kinase activity,[17,18] and induces apoptosis by suppressing surviving gene expression and protein stability and activating the mitochondrial apoptosis pathway.[17] $M_4N$ is able to reverse the multidrug resistance by inhibiting the Sp1-regulated $MDR_1$, gene expression and preventing the synthesis of p-glycoprotein (Pgp).[24] To investigate the effect of water soluble NDGA derivative $P_4N$ on growth of the transformed cells, four cell lines, Vero cell (African green monkey kidney cells), human liver cancer line Hep3B, prostate cancer cell line HT29, and human breast cancer line MCF-7 were selected for testing. The Vero cell line is aneuploid. Although these cells can grow indefinitely in culture, they generally do not form tumors in immunosuppressed mice, while the three selected human cancer cell lines readily do. $P_4N$ (48 hrs, 37° C.) treatment was found to be extremely effective in inhibition of all four rapidly dividing transform cells (FIG. 11) while much less so toward stationary phase vero cells (FIG. 11A).

The presence of $P_4N$ altered the conformation of double stranded deoxyoligonucleotide containing Sp1 binding site '5GGGCGGG3' ($dsOLIGO_{sp}$) by widening its major groove with an increased opening of 2.3 Å (Ref 25, JMB 349, 731-744 2005). Such $P_4N/dsOLIGO_{sp}$ interactions were further supported by 1D and 2D NMR spectroscopy and by uv-melts from the current study. By inducing structural distortion of Sp1 regulated promoters, $P_4N$ makes the cognate site unrecognizable by the Sp1 protein, a key transcription factor for gene expressions in rapidly dividing systems. In addition to inhibiting HIV-1 transactivation, $P_4N$ suppresses HSV-2 replication in a mouse vaginal model when treated locally. Proliferations of three human cancer cell lines, Hep3B, HT-29 and MCF-7 were effectively stopped by $P_4N$ with IC50 of 2 μM, 0.8 μM and 1.4 μM respectively.

In comparison with compounds 6a,b and 7, the ether linkage in compounds 5a-d resulted in much greater stability in aqueous medium. The results of the HIV Tat-regulated transactivation experiments indicated that the piperidine derivative 5b possessed much greater activity than the pyrrolidine derivative 5a. The angle strain in the five-membered rings is greater than that in six-membered rings, which may limit the bioactivity. On the other hand, placement of an oxygen atom at the 4-position in the six-membered ring decreased the anti-HIV transactivation activity; the morpholine derivative 5c ($IC_{50}$=17.34 μM) was less potent than piperidine derivative 5b ($IC_{50}$=0.88 μM). In the morpholine series (cf. 5c and 5d), we found that activity was increased by elongating the spacer from two methylene units to three units (Scheme 1 and Table 1). Among these NDGA derivatives, compound 5b ($P_4N$) showed most potent activity in suppressing HIV Tat-regulated transactivation. It was able to inhibit HSV-2 infection with no apparent sign of toxicity in female mice treated locally with 10 mM (FIG. 10). In addition, $P_4N$ was found to effectively eliminate the growth of three human tumor cells at concentrations<5 μM (FIG. 11).

All publications cited herein are hereby incorporated by reference.

REFERENCES

1. Trang, T.; Stutak, M.; Quirion, R.; Jhamandas, K. *Br. J. Pharmacol.* 2003, 140, 295-304.
2. Nakadate, T. Jpn. *J. Pharmacol.* 1989, 49, 1-9.
3. Hausott, B.; Greger, H.; Marian, B. *J. Cancer Res. Clin. Oncol.* 2003, 129, 569-576.
4. Fujiwara, T.; Misumi, Y.; Ikehara, Y. *Biochem. Biophys. Res. Commun.* 2003, 301, 927-933.
5. (a) Cheng, J. S.; Jan, C. R. *Toxicol. In Vitro* 2002, 16, 485-490. (b) Wang, J. L.; Chang, H. J.; Tseng, L. L.; Liu, C. P.; Lee, K. C.; Chou, K. J.; Cheng, J. S.; Lo, Y. K.; Su, W.; Law, Y. P.; Chen, W. C.; Chan, R. C.; Jan, C. R. *Pharmacol.*

Toxicol. 2001, 89, 301-305. (c) Su, W.; Tseng, L. L.; Lin, M. C.; Chang, H. J.; Lee, K. C.; Chou, K. J.; Lo, Y. K.; Cheng, J. S. Chang, H. T.; Wang, J. L.; Liu, C. P.; Chen, W. C.; Jan, C. R. *Neurochem. Int.* 2002, 40, 249-254. (d) Huang, J. K.; Chen, W. C.; Huang, C. J.; Hsu, S. S.; Chen, J. S.; Cheng, H. H.; Chang, H. T.; Jiann, B. P.; Jan, C. R. *Life Sciences* 2004, 75, 2341-2351.
6. Yamamura, H.; Nagano, N.; Hirano, M.; Muraki, K.; Watanabe, M. Imaizumi, Y. *J. Pharmacol. Exp. Ther* 1999, 291, 140-146.
7. Ono, K.; Hasegawa, K.; Yoshiike, Y.; Takashima, A.; Yamada, M.; Naiki, H. *J. Neurochem.* 2002, 81, 434-440.
8. Lee, C. H.; Jang, Y. S.; Her, S. J.; Moon, Y. M.; Baek, S. J.; Eling, T. *Exp. Cell. Res.* 2003, 289, 335-341.
9. Hwu, J. R.; Tseng, W. N.; Gnabre, J.; Giza, P.; Huang, R. C. *J. Med. Chem.* 1998, 41, 2994-3000.
10. Huang, R. C.; Li, Y.; Giza, P. E.; Gnabre, J. N.; Abd-Elazem, I. S.; King, K. Y.; Hwu, J. R. *Antiviral Res.* 2003, 58, 57-64.
11. King, K. Y.; Hakimelahi, G. H.; Huang, R. C.; Hwu, J. R. *J. Genetics Mol. Biol.* 2002, 13, 248-257.
12. Gnabre, J. N.; Brady, J. N.; Clanton, D. J.; Ito, Y.; Dittmer, J.; Bates, R. B.; Huang, R. C. *Proc. Natl. Acad. Sci. USA* 1995, 92, 11239-11243.
13. Gnabre, J.; Ito, Y.; Ma, Y.; Huang, R. C. *J. Chromatogr. A* 1996, 719, 353-364
14. Chen, H.; Teng, L.; Li, J.; Park, R.; Mold, D. E.; Gnabre, J.; Hwu, J. R.; Tseng, W. N.; Huang, R. C. *J. Med. Chem.* 1998, 41, 3001-3007.
15. Park, R.; Giza, P. E.; Mold, D. E.; Huang, R. C. *Antiviral Res.* 2003, 58, 35-45.
16. Craigol, J.; Callahan, M.; Huang, R. C.; DeLucia, A. *Antiviral Res.* 2000, 47, 19-28.
17. Chang, C.-C.; Heller, J. D.; Kuo, J.; Huang, R. C. *Proc. Natl. Acad. Sci. USA* 2004, 101, 13239-13244.
18. Heller, J. D.; Kuo, J.; Wu, T. C.; Kast, W. M.; Huang, R. C. *Cancer Res.* 2001, 61, 5499-5504.
19. Berger, J.; Hauber, J.; Hauber, R.; Geiger, R.; Cullen, B. *Gene* 1988, 66, 1.
20. Petty, H. R. *Molecular Biology of Membranes*; Plenum Press: New York, 1993; Chapter 6.
21. Dohm, J. A.; Hsu, M. H.; Hsu, J. R.; Huang, R. C.; Moudrianakis, E. N.; Lattman, E. E. *JMB,* 2005, 349, 731-744.
22. Park, R.; Chang, C. C.; Liang, Y. C.; Chung, Y.; Henry, R. A.; Lin, E.; Mold, D. E.; Huang, R. C. *Clin. Cancer Res.,* 2005, 11(12), 4601-4609.
23. Erimos Pharmaceuticals data on file.
24. Chang, C. C.; Liang, Y. C.; Kultz, A.; Hsu, C. I.; Lin, C. F.; Mold, D. E.; Chou, T. C.; Lee, Y. C.; Huang R. C. Published on line Mar. 17, 2006 *Cancer Chemotherapy and Pharmacology.*

We claim:

1. A compound of formula

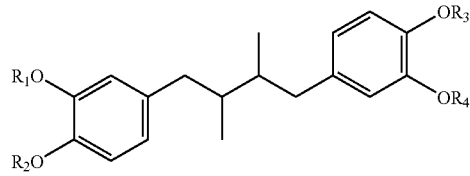

wherein $R_1$-$R_4$ are independently selected from the group consisting of:
(a) a straight chain or branched lower alkyl group substituted with a nitrogen-containing ring group of five to seven members; and
(b) in combination with the O attached to the phenyl ring, a $C_1$-$C_3$ straight chain or branched carbonate group;
or a salt of the compound.

2. The compound of claim 1, wherein the straight chain or branched lower alkyl group is terminally substituted with a nitrogen-containing ring group of five to seven members.

3. The compound of claim 1, wherein the nitrogen-containing ring group of five to seven members is selected from the group consisting of a pyrrolidino, piperidino, or morpholino group.

4. The compound of claim 1 that is selected from the group consisting of
meso-2,3-dimethyl-1,4-bis(3,4-[2-(pyrrolidino)ethoxyphenyl])butane,
meso-2,3-dimethyl-1,4-bis(3,4-[2-(piperidino)ethoxyphenyl])butane,
meso-2,3-dimethyl-1,4-bis(3,4-[2-(morpholino)ethoxyphenyl])butane,
meso-2,3-dimethyl-1,4-bis(3,4-[3-(morpholino)propoxyphenyl])butane,
meso-2,3-dimethyl-1,4-bis[3,4-(phenyl piperidine-1-carboxylate)]butane, and
meso-2,3-dimethyl-1,4-bis[3,4-(methyl phenyl carbonate)]butane,
and salts thereof.

5. A pharmaceutical composition comprising a pharmaceutically acceptable carrier or excipient and at least one compound of formula

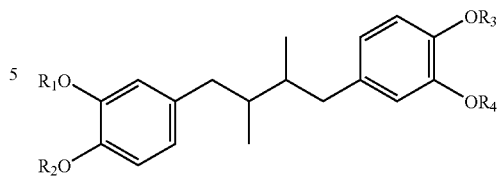

wherein $R_1$-$R_4$ are independently selected from the group consisting of:
(a) a straight chain or branched lower alkyl group substituted with a nitrogen-containing ring group of five to seven members; and
(b) in combination with the O attached to the phenyl ring, a $C_1$-$C_6$ straight chain or branched carbonate group;
or a salt of the compound.

6. The pharmaceutical composition of claim 5, wherein the straight chain or branched lower alkyl group is terminally substituted with a nitrogen-containing ring group of five to seven members.

7. The pharmaceutical composition of claim 5, wherein the nitrogen-containing ring group of five to seven members is selected from the group consisting of a pyrrolidino, piperidino, and morpholino group.

8. The pharmaceutical composition of claim 5, wherein the composition is formulated for a route of administration selected from the group consisting of intranasal administration; oral administration; inhalation administration; subcutaneous administration; transdermal administration; intradermal administration; intra-arterial administration, with or without occlusion; intracranial administration; intraventricular administration; intravenous administration; buccal administration; intraperitoneal administration; intraocular administration; intramuscular administration; implantation administration; topical administration; and central venous administration.

9. The pharmaceutical composition of claim 5, wherein the pharmaceutically acceptable carrier or excipient comprises a carrier or excipient selected from the group consisting of dimethyl sulfoxide (DMSO), phosphate buffered saline, saline, a lipid based formulation, a liposomal formulation, a nanoparticle formulation, a micellar formulation, a water soluble formulation, and a biodegradable polymer.

10. A kit comprising the pharmaceutical composition of claim 5.

* * * * *